United States Patent
Wegman et al.

(10) Patent No.: US 6,521,783 B1
(45) Date of Patent: Feb. 18, 2003

(54) PROCESSES FOR PREPARING OXYGENATES

(75) Inventors: Richard William Wegman, South Charleston, WV (US); David McNeill Somerville, Hurricane, WV (US); Barry Brent Fish, Nitro, WV (US); Raymond Edwin Rooks, Cross Lanes, WV (US); Chinsoo Stephen Lee, Charleston, WV (US); Paul Frank Bryan, Mt. Vernon, WV (US); William J. Bartley, Charleston, WV (US); David Michael Anthony Minahan, Nitro, WV (US); Fungau Ho, Charleston, WV (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 132 days.

(21) Appl. No.: 09/613,275

(22) Filed: Jul. 10, 2000

Related U.S. Application Data

(63) Continuation-in-part of application No. 09/360,097, filed on Jul. 23, 1999, now abandoned, which is a continuation-in-part of application No. 09/220,438, filed on Dec. 24, 1998, now Pat. No. 6,127,432, which is a continuation-in-part of application No. 09/192,134, filed on Nov. 13, 1998, now abandoned, which is a continuation-in-part of application No. 09/015,240, filed on Jan. 29, 1998, now abandoned.

(51) Int. Cl.[7] .............................................. C07C 67/36
(52) U.S. Cl. .................. 560/232; 560/97; 560/114; 560/206; 560/233; 562/406; 562/497; 562/483; 562/517; 562/519; 562/890; 562/891; 568/909
(58) Field of Search .................. 562/519, 483, 562/890, 891, 406, 497, 517; 568/909; 560/232, 97, 114, 206, 233

(56) References Cited

U.S. PATENT DOCUMENTS

| | | | |
|---|---|---|---|
| 5,189,203 A | 2/1993 | Hansen et al. ............... 560/232 |
| 5,218,140 A | 6/1993 | Wegman ..................... 560/232 |
| 5,286,900 A | 2/1994 | Hansen et al. .............. 560/232 |
| 5,316,627 A | * 5/1994 | Hammer ...................... 203/34 |
| 5,330,955 A | 7/1994 | Wegman ..................... 502/210 |
| 5,420,345 A | 5/1995 | Smith ........................ 562/519 |
| 5,502,248 A | * 3/1996 | Funk et al. ................. 562/606 |
| 5,659,077 A | 8/1997 | Macfarlan ................ 562/512.2 |
| 5,663,429 A | 9/1997 | Yamaseki et al. ........... 562/519 |
| 5,780,383 A | 7/1998 | Hollstein et al. ........... 502/324 |

FOREIGN PATENT DOCUMENTS

| | | |
|---|---|---|
| EP | 0685259 | 12/1995 |
| JP | 6178933 | 8/1986 |
| JP | 62148437 | 7/1987 |
| JP | 62148438 | 7/1987 |
| JP | 01294643 | 11/1989 |

OTHER PUBLICATIONS

Arata, Kazushi, "Preparation of superacids by metal oxides for reactions of butanes and pentanes", Applied Catalysis A: General 146 (1996) 3–32.

Momose, Hiroo et al., "Vapor–Phase Direct Hydration of Ethylene over Zirconium Tungstate Catalyst", Journal of Catalysis 77, 23–31 (1982).

Iglesia, Enrique et al., "Selective Isomerization of Alkanes on Supported Tungsten Oxide Acids", Studies in Surface Science and Catalysis, vol. 101 (1996) 533–542, Elsevier Science B.V.

Hino, Makoto et al., "Synthesis of Esters from Acetic Acid with Methanol, Ethanol, Propanol, Butanol, and Isobutyl Alcohol Catalyzed by Solid Superacid[1]", Chemistry Letters, pp. 1671–1672, The Chemical Society of Japan (1981).

Yamaguchi, Tsutomu, "Recent Progress in Solid Superacid", Applied Catalysis, 61 (1990) 1–25, Elsevier Science Publishers B.V., Amsterdam—Printed in the Netherlands.

Larsen, Gustavo et al., "Tungsta and Plantinum–Tungsta Supported on Zirconia Catalysts for Alkane Isomerization", Studies in Surface Science and Catalysis, vol. 101, Elsevier Science B.V. (1996), 543–551.

Sardesai, Abhay et al., "Catalytic Synthesis of Methyl Acetate from Dimethyl Ether using Heteropoly Acid Catalyst", (1998) Annual Meeting Technical Program—AIChE.

* cited by examiner

Primary Examiner—Jafar Parsa
(74) Attorney, Agent, or Firm—Warren K. Volles

(57) ABSTRACT

This invention relates in part to a processes for the conversion of a feedstock stream comprising carbon monoxide and hydrogen to a product stream comprising at least one of an ester, acid, acid anhydride and mixtures thereof. This invention also relates in part to processes for converting an alcohol and/or ether feedstock to oxygenated products, e.g., esters, acids, acid anhydrides and mixtures thereof. The processes and catalysts are especially suitable for the production of acetic acid and methyl acetate from a synthesis gas feedstock or from an alcohol and/or ether feedstock.

15 Claims, 14 Drawing Sheets

PROCESSES FOR PREPARING OXYGENATES

This application is a continuation-in-part of U.S. patent application Ser. No. 09/360,097, filed Jul. 23, 1999 now abandoned which is a continuation-in-part of U.S. patent application Ser. No. 09/220,438, filed Dec. 24, 1998 issued as U.S. Pat. No. 6,127,432 which is a continuation-in-part of U.S. patent application Ser. No. 09/192,134, filed Nov. 13, 1998, now abandoned which is a continuation-in-part of U.S. patent application Ser. No. 09/015,240, filed Jan. 29, 1998 now abandoned.

BRIEF SUMMARY OF THE INVENTION

Technical Field

This invention relates to processes for converting carbon monoxide- and hydrogen-containing feedstocks, e.g., synthesis gas, to oxygenated products, e.g., esters, acids, acid anhydrides and mixtures thereof, and to processes for converting alcohol- and/or ether-containing feedstocks to oxygenated products, e.g., esters, acids, acid anhydrides and mixtures thereof.

BACKGROUND OF THE INVENTION

It is known that carboxylic esters, acids, anhydrides and mixtures thereof can be prepared from feedstock comprising carbon monoxide and hydrogen gases by first forming an alcohol, such as methanol, and the corresponding ether (e.g., dimethyl ether), according to the theoretical reaction:

$$2CO+4H_2=2CH_3OH \leftrightarrow (CH_3)_2O+H_2O$$

in the presence of a known alcohol conversion catalyst, and then separately converting the alcohol and/or ether in the presence of a known carbonylation catalyst into esters, acids, anhydrides and mixtures thereof containing one carbon atom more than the starting alcohol and ether, for example (theoretically):

$$CH_3OH+CO=CH_3COOH$$

or $$(CH_3)_2O+2CO+H_2O=2CH_3COOH$$

or $$CH_3OH+(CH_3)_2O+3CO+H_2O=3CH_3COOH$$

Currently, commercial processes for the production of carboxylic acids from the carbonylation of an alcohol, ether and/or alcohol/ether mixture employ halide, e.g., iodide, promoters which are essential to obtain an acceptable level of catalyst activity. See, for example, U.S. Pat. Nos. 5,663,430, 5,750,007 and 5,672,743. Halide promoters are highly corrosive, requiring the use of exotic metals in the construction of the reaction vessels and expensive processing equipment (e.g., separation and refining equipment) to recover the homogeneous promoter from the product stream.

Known catalytic carbonylation processes for producing oxygenates which do not employ halide promoters are described in U.S. Pat. Nos. 5,218,140 and 5,330,955. Such processes involve the carbonylation of one or more alcohols or ethers to esters and carboxylic acids. The processes are carried out in the vapor state over a solid catalyst comprising a polyoxometalate anion in which the metal is at least one selected from Groups 5 and 6 (such as molybdenum, tungsten, vanadium, niobium, chromium and tantalum) complexed with at least one Group 8, 9 or 10 cation (such as Fe, Ru, Os, Co, Rh, Ir, Ni, Pd and Pt).

The oxygenates industry, particularly the acetic acid industry, would benefit significantly from a process that would simplify and/or eliminate complex, expensive equipment while simultaneously enabling more control over reaction rates and product selectivity. A solution enabling these advantages would provide a highly desirable industrial advance. Improved carbonylation catalysts for making oxygenates with respect to catalyst stability and carbonylation activity and selectivity would also be a highly desirable industrial advance.

DISCLOSURE OF THE INVENTION

This invention relates in part to a process for converting a feedstock stream comprising carbon monoxide and hydrogen to a product stream comprising at least one of an ester, acid, acid anhydride and mixtures thereof which comprises reacting said feedstock stream in the presence of a catalyst comprising an alcohol synthesis catalytic component and an alcohol carbonylation catalytic component, the composition of the components being different from one another and the composition of the alcohol carbonylation catalytic component comprising a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, or mixtures thereof, and in the absence of a halide promoter, under conditions of temperature and pressure sufficient to produce said product stream. This process is preferably a gas or vapor phase reaction of synthesis gas to produce oxygenates therefrom, and is especially advantageous for the production of acetic acid and/or methyl acetate utilizing a single reaction vessel.

This invention also relates in part to a process for converting a feedstock stream comprising carbon monoxide and hydrogen to a product stream comprising at least one of an ester, acid, acid anhydride and mixtures thereof which comprises (a) reacting said feedstock stream in the presence of a catalyst under conditions of temperature and pressure sufficient to produce at least one of an alcohol, ether and mixtures thereof and (b) reacting carbon monoxide and said at least one of an alcohol, ether and mixtures thereof in the presence of a catalyst comprising a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, or mixtures thereof, and in the absence of a halide promoter, under conditions of temperature and pressure sufficient to produce said product stream. This process is preferably a gas or vapor phase reaction, and is especially advantageous for the production of acetic acid and/or methyl acetate utilizing separate reaction vessels for steps (a) and (b).

This invention further relates in part to a process for converting a feedstock stream comprising at least one of an alcohol and ether and mixtures thereof to a product stream comprising at least one of an ester, acid, acid anhydride and mixtures thereof which comprises reacting said feedstock stream and carbon monoxide in the presence of a catalyst comprising a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, or mixtures thereof, and in the absence of a halide promoter, under conditions of temperature and pressure sufficient to produce said product stream. This process is preferably a gas or vapor phase reaction, and is especially advantageous for the production of acetic acid and/or methyl acetate utilizing one or more reaction vessels.

This invention yet further relates in part to a process for converting a feedstock stream comprising at least one of an alcohol and ester and mixtures thereof to a product stream comprising at least one of an ether, acid, acid anhydride and mixtures thereof which comprises reacting said feedstock stream in the presence of a catalyst comprising an ester hydrolysis catalytic component and an alcohol dehydration catalytic component under conditions of temperature and pressure sufficient to produce said product stream. This process is preferably a gas or vapor phase reaction of an alcohol and ester to produce an ether and acid therefrom, and is especially advantageous for the production of acetic acid and/or dimethyl ether utilizing a single reaction vessel, e.g., a coupled hydrolysis/dehydration reactor.

The processes and catalysts of this invention are particularly unique in that they enable the production of oxygenates from carbon monoxide- and hydrogen-containing feedstocks or alcohol- and/or ether-containing feedstocks in one or more reactors and in which no halides are required in the liquid or vapor phases of the feedstock streams and/or recycle streams of the processes, thus providing substantial economic benefits in the design of equipment to carry out the processes. Moreover, the multicomponent catalysts of this invention enable substantial control over the composition of the reaction product simply by varying the composition of one component of the catalyst and/or its concentration relative to the other component. Further, the processes and catalysts of this invention enable the production of oxygenates under one or more sets of reaction conditions. The carbonylation catalysts of this invention provide improved catalyst stability and improved carbonylation activity and selectivity as described herein.

DETAILED DESCRIPTION

The following more detailed description of preferred embodiments of this invention is not intended to limit the scope of the invention in any respect as the processes and catalysts may be utilized for the manufacture of other acids, esters, anhydrides and mixtures thereof using the concepts heretofore and hereafter fully and adequately disclosed.

An embodiment of this invention involves a process for converting a feedstock stream comprising carbon monoxide and hydrogen to a product stream comprising at least one of an ester, acid, acid anhydride and mixtures thereof which comprises reacting the carbon monoxide and hydrogen in the presence of a catalyst comprising an alcohol synthesis catalytic component, an alcohol dehydration catalytic component and an alcohol/ether carbonylation catalytic component, the composition of the components being different from one another, under conditions of temperature and pressure sufficient to produce said product stream. A unique embodiment of this invention involves a coupled alcohol synthesis and alcohol dehydration configuration, and also this configuration coupled with carbonylation. An illustrative process scheme of this embodiment is set forth in FIG. 1.

Figure 1:
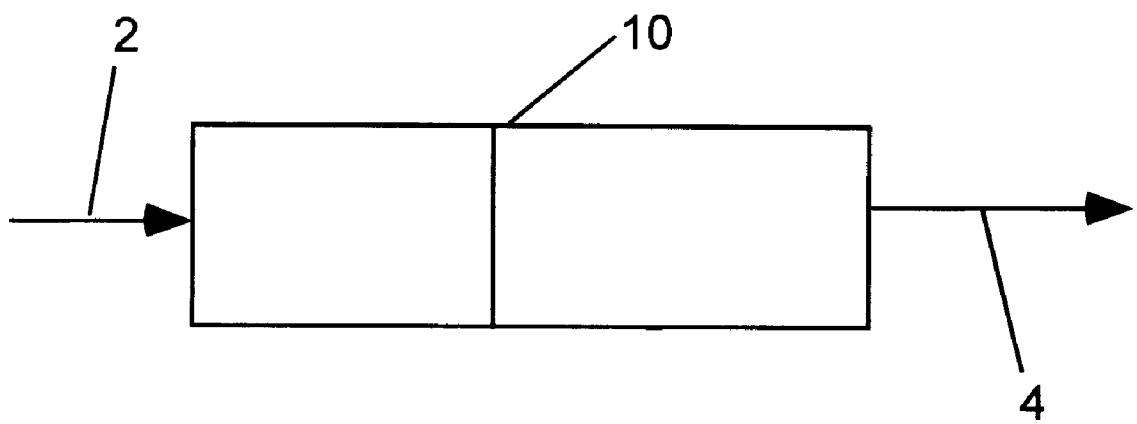
FIG. 1 is a schematic representation of a one-reactor process flow diagram to make acetic acid from a feedstock gaseous mixture comprising carbon monoxide and hydrogen gases, e.g., synthesis gas.

In FIG. 1, which is a simplified flow diagram of an embodiment of this invention involving methanol and dimethyl ether production before carbonylation in a single reactor, a one-reactor process for the preparation of acetic acid from a synthesis gas feed stream is shown. The synthesis gas feed stream is supplied from a synthesis gas generation unit via line 2 to reactor 10 which contains a first and second compartment. The synthesis gas feed stream can have a hydrogen:carbon monoxide molar ratio of from about 20:1 to about 1:20 and a gas hourly space velocity (liters of feedstock/hr/liter of catalyst) of from about 1 to about 30,000 hour$^{-1}$. The first compartment of reactor 10 contains an alcohol synthesis catalyst, e.g., Cu—Zn, Zn—Cr or Pd—SiO$_2$, and an alcohol dehydration catalyst, e.g., an acidic solid such as gamma-alumina, silica, certain phosphoric acid derivatives or a super acid not containing a Group VIII metal, which can be configured as a single bed or layered or intimate mixture. The weight ratio of alcohol synthesis catalyst:alcohol dehydration catalyst can range from about 20:1 to about 1:20. The first compartment of reactor 10 is maintained at pre-selected reaction conditions of temperature and pressure, e.g., a temperature from about 100° C. to about 400° C. and a pressure from about 1 to about 10,000 psig, so that a vapor phase reaction takes place in which the feedstock gas is converted first to methanol and at least a portion of the methanol then converted to dimethyl ether and water. The purpose of this is to increase synthesis gas conversion in the methanol producing step. The methanol, dimethyl ether and water are fed to the second compartment of reactor 10, which contains a carbonylation catalyst, and this compartment is maintained at pre-selected reaction conditions of temperature and pressure so that a vapor phase reaction takes place in which the feedstock dimethyl ether and methanol is converted to oxygenates, most preferably containing a large fraction of acetic acid. The carbonylation catalyst is capable of carbonylating methanol and/or dimethyl ether. The concentration of carbonylation catalyst, alcohol synthesis catalyst and alcohol dehydration catalyst is not narrowly critical and will depend on the desired productivity and other reaction variables. The hydrogen partial pressure in the second compartment of reactor 10 is sufficient to impart stabilization to the carbonylation catalyst. The product stream exits the reactor 10 via line 4 and enters a refining unit (not shown). The product stream can be refined to desired purity by methods described herein. The refining unit is controlled so that a product stream consisting essentially of acetic acid is removed from the refining unit and recovered essentially free of esters, anhydrides, and other byproducts. The gaseous and liquid residuals are removed from the refining unit and recycled to the synthesis gas generation unit and/or reactor 10. A purge stream may be used to control the buildup of inerts.

The advantages of conducting a one-reactor process as depicted by FIG. 1 include a high conversion per pass of synthesis gas, simplified reaction system, reduced capital investment (one reactor vs. two), better heat integration (in a furnace reactor the different heating zones of the furnace can be used to optimize reactor heating; in a liquid heated reactor the heating fluid can run co-current or counter current to optimize the two reaction zones), and a mixed bed catalyst will shift the methanol equilibrium and can markedly decrease the reactor size.

Alternatively, the process depicted in FIG. 1 may be conducted in a two-reactor scheme. Such a two-reactor scheme may be operated in a manner similar to FIG. 1 with the exception that the alcohol synthesis/dehydration and carbonylation occur in separate reactors. This embodiment involves a process for converting a feedstock stream comprising carbon monoxide and hydrogen to a product stream comprising at least one of an ester, acid, acid anhydride and mixtures thereof which comprises (a) feeding at least a portion of said feedstock stream to an alcohol/ether synthesis reaction zone, (b) reacting in the alcohol/ether synthesis reaction zone said carbon monoxide and hydrogen in the presence of a catalyst comprising an alcohol synthesis catalytic component and an alcohol dehydration catalytic component under conditions of temperature and pressure sufficient to produce an ether-containing stream comprising a mixture of an ether and an alcohol, (c) withdrawing said ether-containing stream from said alcohol/ether synthesis reaction zone and feeding at least a portion of the withdrawn ether-containing stream to a carbonylation reaction zone, and (d) reacting in said carbonylation reaction zone carbon monoxide and said ether-containing stream in the presence of a catalyst comprising a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, or mixtures thereof, under conditions of temperature and pressure sufficient to produce said product stream. The methanol/dimethyl ether, water and unreacted synthesis gas may be treated to remove hydrogen prior to entering the carbonylation reactor. However, as described herein, the carbonylation reaction is preferably conducted in the presence of a stabilizing amount of hydrogen, i.e., an amount sufficient to impart stabilization to the carbonylation catalyst.

The advantages of conducting a two-reactor process include a high conversion per pass of synthesis gas and methanol, can operate the methanol/dimethyl ether catalyst at optimal conditions, catalyst change out simplified, can adjust synthesis gas ratio going into carbonylation reactor, can selectively recycle streams to alcohol synthesis/dehydration reactor or carbonylation reactor, carbon dioxide exiting a synthesis gas generation unit can go entirely to methanol synthesis/dehydration reactor where it is mostly consumed, independent operating conditions/controls for each reactor, each catalyst can be replaced at separate times, materials of construction costs can be reduced because alcohol synthesis/dehydration reactor can be carbon steel and carbonylation reactor can be stainless steel, and a simplified reaction system.

Another embodiment of this invention involves a process for converting a feedstock stream comprising carbon monoxide and hydrogen to a product stream comprising at least one of an ester, acid, acid anhydride and mixtures thereof which comprises (a) splitting said feedstock stream into a first feedstock stream and a second feedstock stream, (b) feeding at least a portion of said first feedstock stream to an alcohol and/or ether synthesis reaction zone and said second feedstock stream to a gas separation zone, (c) reacting in the alcohol and/or ether synthesis reaction zone said carbon monoxide and hydrogen in the presence of an alcohol and/or ether synthesis catalyst under conditions of temperature and pressure sufficient to produce an alcohol and/or ether-rich stream comprising at least one of an alcohol and ether and mixtures thereof, (d) withdrawing said alcohol and/or ether-rich stream and unreacted carbon monoxide and hydrogen from said alcohol and/or ether synthesis reaction zone and feeding at least a portion of the withdrawn alcohol and/or ether-rich stream and carbon monoxide and hydrogen to a liquid/gas separation zone, (e) withdrawing from the liquid/gas separation zone an overhead fraction comprising said carbon monoxide and hydrogen and optionally recycling at least a portion of the withdrawn overhead fraction to said alcohol and/or ether synthesis reaction zone, (f) withdrawing from the liquid/gas separation zone a bottoms fraction comprising said alcohol and/or ether-rich stream and feeding at least a portion of the alcohol and/or ether-rich stream to a carbonylation reaction zone, (g) withdrawing from the gas separation zone a first fraction comprising a hydrogen-rich stream and a second fraction comprising a carbon monoxide-rich stream and feeding at least a portion of said carbon monoxide-rich stream to said carbonylation reaction zone, and (h) reacting in said carbonylation reaction zone said carbon monoxide-rich stream and said alcohol and/or ether-rich stream in the presence of a catalyst comprising a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, or mixtures thereof, under conditions of temperature and pressure sufficient to produce said product stream. An illustrative process scheme of this embodiment is set forth in FIG. 2.

Figure 2:
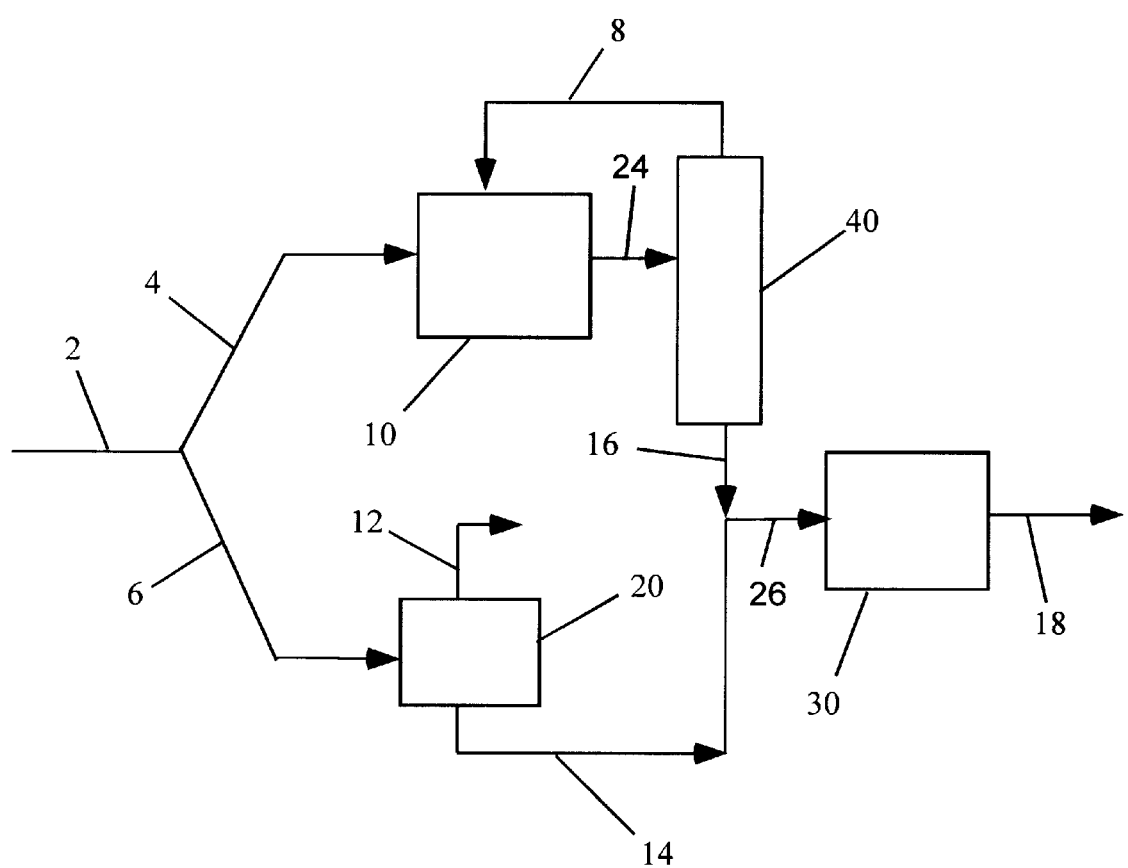
FIG. 2 is a schematic representation of a process flow diagram to make acetic acid from a feedstock gaseous mixture comprising carbon monoxide and hydrogen gases, e.g., synthesis gas.

In FIG. 2, which is a simplified flow diagram of an embodiment of this invention involving separation of synthesis gas in parallel to methanol synthesis, a process for the preparation of acetic acid from a synthesis gas feed stream is shown. The synthesis gas feed stream is supplied from a synthesis gas generation unit via line 2 and is split into two streams, i.e., lines 4 and 6. The synthesis gas feed stream can have a hydrogen:carbon monoxide molar ratio of from about 20:1 to about 1:20 and a gas hourly space velocity of from about 1 to about 30,000 hour$^{-1}$. One synthesis gas stream is fed via line 4 to an alcohol and/or ether synthesis reactor 10. Reactor 10 contains an alcohol synthesis catalyst and optionally an alcohol dehydration catalyst and is maintained at pre-selected reaction conditions of temperature and pressure, e.g., a temperature from about 100° C. to about 400° C. and a pressure from about 1 to about 10,000 psig, so that a reaction, e.g., vapor phase, liquid phase or slurry, takes place in which the feedstock gas is converted to methanol and/or dimethyl ether. Methanol and/or dimethyl ether and unreacted synthesis gas are fed via line 24 to a liquid/gas separator 40 and unreacted synthesis gas is recycled back via line 8 to alcohol and/or ether synthesis reactor 10. The methanol and/or dimethyl ether is fed via line 16 to carbonylation reactor 30. The other synthesis gas stream is fed via line 6 to a gas separator 20 in which carbon monoxide is separated from hydrogen. Hydrogen is removed via line 12 and a carbon monoxide-rich stream (carbon monoxide:hydrogen molar ratio of greater than about 1:1 to about 1000:1) is fed via line 14 to carbonylation reactor 30. The removal of hydrogen limits the amount of hydrogen entering the carbonylation reactor 30 and thus helps to improve selectivity by reducing hydrocarbon formation. However, as described herein, the carbonylation reaction is preferably conducted in the presence of a stabilizing amount of hydrogen, i.e., an amount sufficient to impart stabilization to the carbonylation catalyst. The carbonylation reactor 30 contains an alcohol and/or ether carbonylation catalyst and is maintained at pre-selected reaction conditions of temperature and pressure, e.g., a temperature from about 100° C. to about 400° C. and a pressure from about 1 to about 10,000 psig, so that a vapor phase reaction takes place in which the methanol and/or dimethyl ether and carbon monoxide feedstocks are converted to oxygenates, most preferably containing a large fraction of acetic acid. The alcohol and/or ether carbonylation catalyst is capable of carbonylating methanol and/or dimethyl ether. The concentration of carbonylation catalyst, alcohol synthesis catalyst and alcohol dehydration catalyst is not narrowly critical and will depend on the desired productivity and other reaction variables. The hydrogen partial pressure in carbonylation reactor 30 is sufficient to impart stabilization to the carbonylation catalyst. The product stream exits the carbonylation reactor 30 via line 18 and enters a refining unit (not shown). The product stream can be refined to desired purity by methods described herein. The refining unit is controlled so that a product stream consisting essentially of acetic acid is removed from the refining unit and recovered essentially free of esters, anhydrides, and other byproducts. The gaseous and liquid residuals are removed from the refining unit and recycled to the synthesis gas generation unit and/or reactor 10. The product stream exiting the carbonylation reactor via line 18 can be refined by methods known to the art. For example, lights can be separated first and the resulting crude stream sent to a first distillation zone operated with a base temperature of about 100° C.–270° C. and a pressure of about 1–68 atmospheres. Crude acetic acid is recovered as a tails stream and sent to a polishing column operated at 22–760 mmHg were acetic acid is obtained overhead. A purge stream may be used to control the buildup of inerts.

The advantages of conducting a process as depicted by FIG. 2 include the alcohol and/or ether synthesis reactor 10 and carbonylation reactor 30 can be operated under separate conditions for optimization purposes and recycle streams can be directed to one or both reactors which avoids recycle of all components through the entire reaction system. Low hydrogen to the carbonylation reactor 30 results in less hydrocarbon, e.g., methane, formation. Hydrogen can thus be made available for sale or down stream use. The FIG. 2 process allows better process control because of flexibility in synthesis gas ratio. Carbon dioxide can be recycled to the synthesis gas generation unit and/or alcohol and/or ether synthesis reactor 10.

Another embodiment of this invention involves a process for converting a feedstock stream comprising carbon monoxide and hydrogen to a product stream comprising at least one of an ester, acid, acid anhydride and mixtures thereof which comprises (a) feeding at least a portion of said feedstock stream to an alcohol and/or ether synthesis reaction zone, (b) reacting in the alcohol and/or ether synthesis reaction zone said carbon monoxide and hydrogen in the presence of an alcohol and/or ether synthesis catalyst under conditions of temperature and pressure sufficient to produce an alcohol and/or ether-rich stream comprising at least one of an alcohol and ether and mixtures thereof, (c) withdrawing said alcohol and/or ether-rich stream and unreacted carbon monoxide and hydrogen from said alcohol and/or ether synthesis reaction zone and feeding at least a portion of the withdrawn alcohol and/or ether-rich stream and carbon monoxide and hydrogen to a liquid/gas separation zone, (d) withdrawing from the liquid/gas separation zone an overhead fraction comprising said carbon monoxide and hydrogen and feeding at least a portion of the withdrawn overhead fraction to a gas separation zone, (e) withdrawing from the gas separation zone a first fraction comprising a hydrogen-rich stream and a second fraction comprising a carbon monoxide-rich stream and feeding at least a portion of said carbon monoxide-rich stream to said carbonylation reaction zone, (f) withdrawing from the liquid/gas separation zone a bottoms fraction comprising said alcohol and/or ether-rich stream and feeding at least a portion of the alcohol and/or ether-rich stream to said carbonylation reaction zone, and (g) reacting in said carbonylation reaction zone said carbon monoxide-rich stream and said alcohol and/or ether-rich stream in the presence of a catalyst comprising a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, or mixtures thereof, under conditions of temperature and pressure sufficient to produce said product stream. An illustrative process scheme of this embodiment is set forth in FIG. 3.

Figure 3:
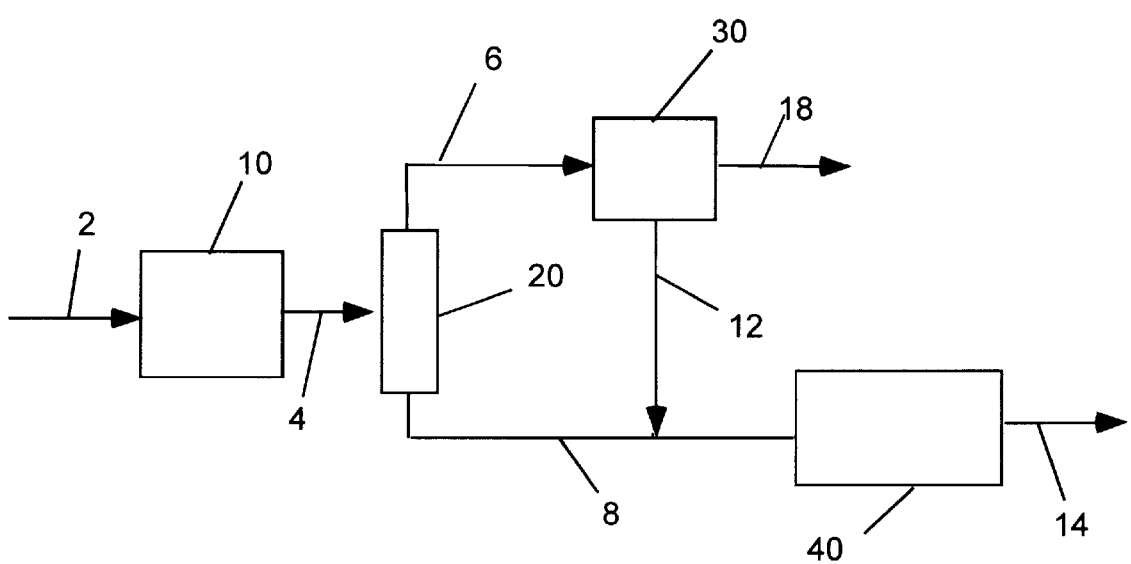
FIG. 3 is a schematic representation of a process flow diagram to make acetic acid from a feedstock gaseous mixture comprising carbon monoxide and hydrogen gases, e.g., synthesis gas.

In FIG. 3, which is a simplified flow diagram of an embodiment of this invention involving separation of synthesis gas after methanol synthesis, a process for the preparation of acetic acid from a synthesis gas feed stream is shown. The synthesis gas feed stream is supplied to alcohol and/or ether synthesis reactor 10 from a synthesis gas generation unit via line 2. The synthesis gas feed stream can have a hydrogen:carbon monoxide molar ratio of from about 20:1 to about 1:20 and a gas hourly space velocity of from about 1 to about 30,000 hour$^{-1}$. Reactor 10 contains an alcohol synthesis catalyst and optionally an alcohol dehydration catalyst and is maintained at pre-selected reaction conditions of temperature and pressure, e.g., a temperature from about 100° C. to about 400° C. and a pressure from about 1 to about 10,000 psig, so that a reaction, e.g., vapor phase, liquid phase or slurry, takes place in which the feedstock gas is converted to methanol and/or dimethyl ether. Methanol and/or dimethyl ether and unreacted synthesis gas are fed via line 4 to a liquid/gas separator 20 and unreacted synthesis gas is fed via line 6 to a gas separator 30 in which carbon monoxide is separated from hydrogen. Hydrogen is removed via line 18 and a carbon monoxide-rich stream containing low levels of hydrogen (carbon monoxide:hydrogen molar ratio of greater than about 1:1 to about 1000:1) is fed via lines 12 and 8 (combined with methanol in line 8) to carbonylation reactor 40. The carbon monoxide-rich stream can be split and added to the separated hydrogen stream (line 18) and recycled back to the alcohol and/or ether synthesis reactor 10. The methanol is fed via line 8 to carbonylation reactor 40. The removal of hydrogen limits the amount of hydrogen entering the carbonylation reactor 40 and thus helps to improve selectivity by reducing hydrocarbon formation. However, as described herein, the carbonylation reaction is preferably conducted in the presence of a stabilizing amount of hydrogen, i.e., an amount sufficient to impart stabilization to the carbonylation catalyst. The carbonylation reactor 40 contains an alcohol and/or ether carbonylation catalyst and is maintained at pre-selected reaction conditions of temperature and pressure, e.g., a temperature from about 100° C. to about 400° C. and a pressure from about 1 to about 10,000 psig, so that a vapor phase reaction takes place in which the methanol and/or dimethyl ether and carbon monoxide feedstocks are converted to oxygenates, most preferably containing a large fraction of acetic acid. The alcohol and/or ether carbonylation catalyst is capable of carbonylating methanol and/or dimethyl ether. The concentration of carbonylation catalyst, alcohol synthesis catalyst and alcohol dehydration catalyst is not narrowly critical and will depend on the desired productivity and other reaction variables. The hydrogen partial pressure in carbonylation reactor 40 is sufficient to impart stabilization to the carbonylation catalyst. The product stream exits the carbonylation reactor 40 via line 14 and enters a refining unit (not shown). The product stream can be refined to desired purity by methods described herein. The refining unit is controlled so that a product stream consisting essentially of acetic acid is removed from the refining unit and recovered essentially free of esters, anhydrides, and other byproducts. The gaseous and liquid residuals are removed from the refining unit and recycled to the synthesis gas generation unit and/or reactor 40. A purge stream may be used to control the buildup of inerts.

The advantages of conducting a process as depicted by FIG. 3 include the carbonylation reactor size can be decreased by limiting the amount of hydrogen feed to it. Low hydrogen to the carbonylation reactor 40 results in less hydrocarbon, e.g., methane, formation. Hydrogen can thus be made available for sale or down stream use.

Another embodiment of this invention involves a process for converting a feedstock stream comprising at least one of an alcohol and ether and mixtures thereof to a product stream comprising at least one of an ester, acid, acid anhydride and mixtures thereof which comprises (a) feeding at least a portion of a first feedstock stream comprising carbon monoxide and a second feedstock stream comprising an alcohol and/or ether to a carbonylation reaction zone, and (b) reacting in said carbonylation reaction zone said carbon monoxide and said alcohol and/or ether in the presence of a catalyst comprising a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, or mixtures thereof, under conditions of temperature and pressure sufficient to produce said product stream. An illustrative process scheme of this embodiment is set forth in FIG. 4.

Figure 4:
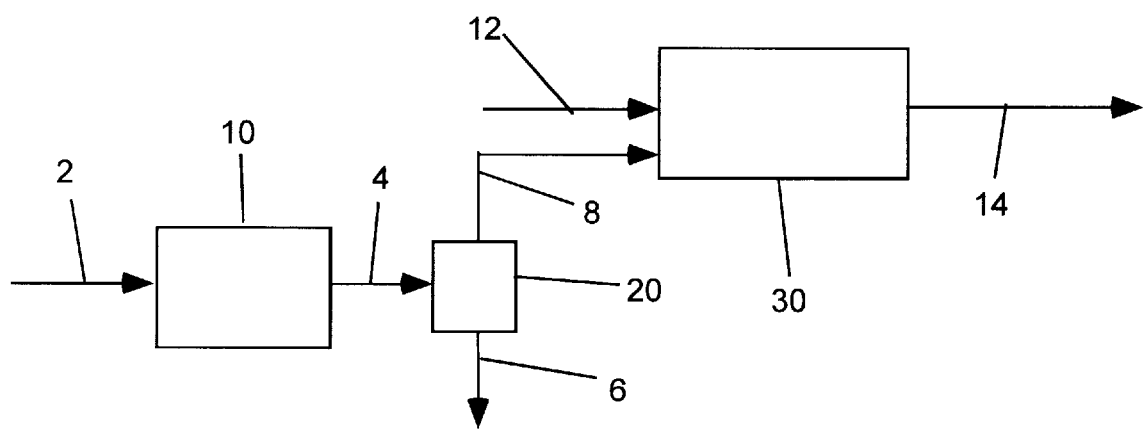
FIG. 4 is a schematic representation of a process flow diagram to make acetic acid from a methanol feedstock and a feedstock gaseous mixture comprising carbon monoxide and hydrogen gases prepared from a hydrocarbon feed to a synthesis gas generation unit.

In FIG. 4, which is a simplified flow diagram of an embodiment of this invention involving methanol and/or dimethyl ether not made in situ, a one-reactor process for the preparation of acetic acid from a synthesis gas feed stream and methanol and/or dimethyl ether feed stream is shown. A hydrocarbon stream, e.g., methane and oxygen, is supplied via line 2 to a synthesis gas generation unit 10 which generates a synthesis gas stream. The synthesis gas stream can have a hydrogen:carbon monoxide molar ratio of from about 20:1 to about 1:20 and a gas hourly space velocity of from about 1 to about 30,000 hour$^{-1}$. The synthesis gas stream exits the synthesis gas generation unit 10 and is fed via line 4 to a gas separator 20 in which carbon monoxide is separated from hydrogen. Hydrogen is removed via line 6 and a carbon monoxide-rich stream (carbon monoxide:hydrogen molar ratio of greater than about 1:1 to about 1000:1) is fed via line 8 to carbonylation reactor 30. The removal of hydrogen limits the amount of hydrogen entering the carbonylation reactor 30 and thus helps to improve selectivity by reducing hydrocarbon formation. However, as described herein, the carbonylation reaction is preferably conducted in the presence of a stabilizing amount of hydrogen, i.e., an amount sufficient to impart stabilization to the carbonylation catalyst. Methanol and/or dimethyl ether is fed to carbonylation reactor 30 via line 12. In this scheme, methanol and/or dimethyl ether is supplied to the carbonylation reactor 30 from an external source, for example, another process unit or obtained commercially. If desired, synthesis gas can be obtained from a different source and fed directly to the carbonylation catalyst. The carbonylation reactor 30 contains an alcohol and/or ether carbonylation catalyst and is maintained at pre-selected reaction conditions of temperature and pressure, e.g., a temperature from about 100° C. to about 400° C. and a pressure from about 1 to about 10,000 psig, so that a vapor phase reaction takes place in which the methanol and carbon monoxide feeds are converted to oxygenates, most preferably containing a large fraction of acetic acid. The concentration of carbonylation catalyst is not narrowly critical and will depend on the desired productivity and other reaction variables. The hydrogen partial pressure in carbonylation reactor 30 is sufficient to impart stabilization to the carbonylation catalyst. The product stream exits the reactor 30 via line 14 and enters a refining unit (not shown). The product stream can be refined to desired purity by methods described herein. The refining unit is controlled so that a product stream consisting essentially of acetic acid is removed from the refining unit and recovered essentially free of esters, anhydrides, and other byproducts. Hydrocarbon byproducts and unreacted materials can be removed from the refining unit and recycled to the synthesis gas generation unit 10 and/or carbonylation reactor 30. A purge stream may be used to control the buildup of inerts.

The advantages of conducting a process as depicted by FIG. 4 include a reduced capital expense due to the synthesis gas generation unit size is reduced due to less synthesis gas requirements, no methanol and/or ether synthesis reactor needed, purchased methanol allows easier control of the overall process, can feed crude (low grade) methanol containing dimethyl ether or other by-products, greater freedom with the synthesis gas generation unit because 2:1 synthesis gas is not required, and can use wider range of feedstock such as naphtha or heavy oils to give closer to 1:1 synthesis gas ratio.

Another embodiment of this invention involves a process for converting a feedstock stream comprising at least one of an alcohol and ether and mixtures thereof to a product stream comprising at least one of an ester, acid, acid anhydride and mixtures thereof which comprises (a) feeding at least a portion of a first feedstock stream comprising carbon monoxide and a second feedstock stream comprising an alcohol and/or ether to a carbonylation reaction zone, (b) reacting in said carbonylation reaction zone the first and second feedstock streams in the presence of a catalyst comprising a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, or mixtures thereof, under conditions of temperature and pressure sufficient to produce a first crude product stream comprising at least one of an ester, acid, acid anhydride, alcohol, ether, water and mixtures thereof, (c) withdrawing said first crude product stream and unreacted carbon monoxide from said carbonylation reaction zone and feeding at least a portion of the withdrawn stream and carbon monoxide to a liquid/gas separation zone, (d) withdrawing from the liquid/gas separation zone an overhead fraction comprising said carbon monoxide and optionally recycling at least a portion of the withdrawn overhead fraction to said carbonylation reaction zone, (e) withdrawing from the liquid/gas separation zone a bottoms fraction comprising said first crude product stream and feeding at least a portion of the withdrawn bottoms fraction to a distillation zone, (f) withdrawing from the distillation zone an overhead fraction comprising an ester and feeding at least a portion of the withdrawn overhead fraction to a hydrolysis reaction zone, (g) reacting in the hydrolysis reaction zone in the presence of an ester hydrolysis catalyst said withdrawn overhead fraction under conditions of temperature and pressure sufficient to produce a second crude product stream comprising at least one of an ester, acid, acid anhydride, alcohol, ether, water and mixtures thereof (containing less ester and more acid than said first crude product stream), (h) withdrawing from the hydrolysis reaction zone said second crude product stream and feeding at least a portion of the withdrawn stream to said distillation zone, (i) optionally withdrawing from the distillation zone a sidedraw fraction comprising an alcohol and/or ether and feeding at least a portion of the withdrawn sidedraw fraction to said carbonylation reaction zone, and (j) withdrawing from the distillation zone a bottoms fraction comprising said product stream. An illustrative process scheme of this embodiment is set forth in FIG. 5.

Figure 5:
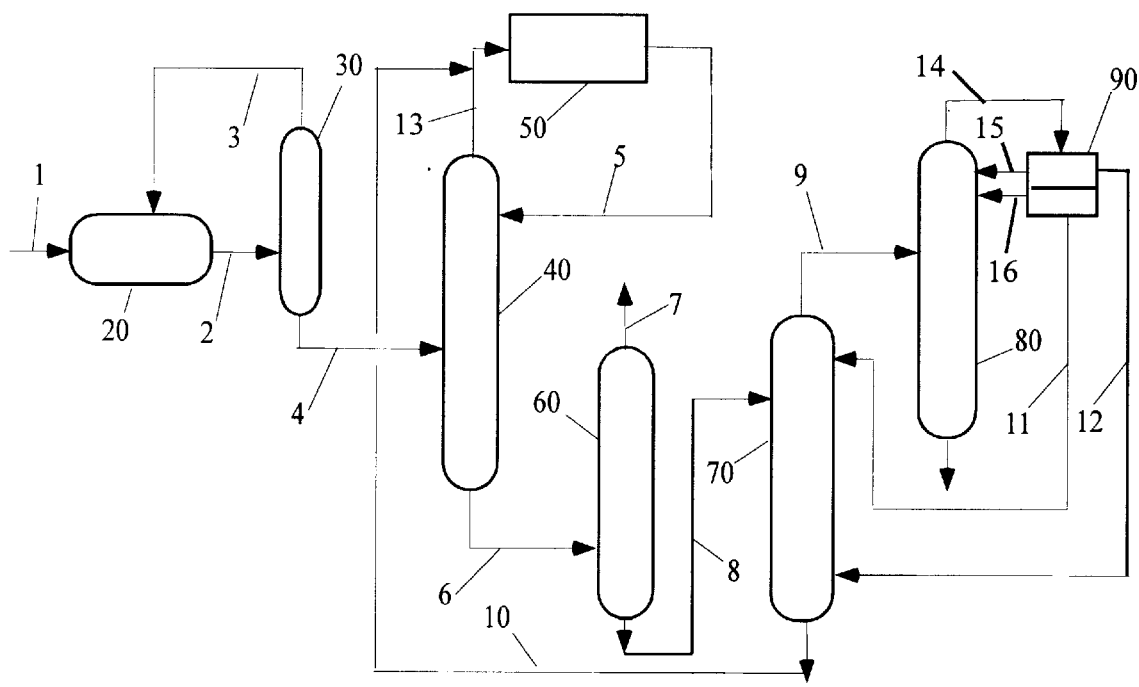
FIG. 5 is a schematic representation of a process flow diagram to make acetic acid from a methanol feedstock and a carbon monoxide-containing feedstock.

In FIG. 5, which is a simplified flow diagram of an embodiment of this invention involving methyl acetate hydrolysis and extraction of acetic acid, a process for the preparation of acetic acid from a carbon monoxide feed stream and methanol and/or dimethyl ether feed stream is shown. Methanol and/or dimethyl ether and a carbon monoxide-containing stream (carbon monoxide:hydrogen molar ratio of about 1000:1 to about 1:1000) are fed to carbonylation reactor 20 via line 1. In this scheme, methanol and/or dimethyl ether is supplied to the carbonylation reactor 20 from an external source, for example, another process unit or obtained commercially. Methanol and/or dimethyl ether can optionally be formed in situ by feeding synthesis gas to a methanol and/or dimethyl ether producing catalyst that is coupled to the carbonylation catalyst either in the same or different reactors. Likewise, carbon monoxide can optionally be formed in situ by feeding a hydrocarbon stream, e.g., methane and oxygen, to a synthesis gas generation unit which generates a synthesis gas stream. The synthesis gas stream exits the synthesis gas generation unit and is fed to a gas separator in which carbon monoxide is separated from hydrogen. If desired, either methanol, dimethyl ether and/or synthesis gas can be obtained from a different source and fed directly to the carbonylation catalyst. The carbon monoxide stream can have a hydrogen:carbon monoxide molar ratio of from about 20:1 to about 1:20 and a gas hourly space velocity of from about 1 to about 30,000 hour$^{-1}$. The carbonylation reactor 20 contains an alcohol and/or ether carbonylation catalyst and is maintained at pre-selected reaction conditions of temperature and pressure, e.g., a temperature from about 100° C. to about 400° C. and a pressure from about 1 to about 10,000 psig, so that a vapor phase reaction takes place in which the methanol and/or dimethyl ether and carbon monoxide feeds are converted to oxygenates, most preferably containing a large fraction of acetic acid. The hydrogen partial pressure in carbonylation reactor 20 is sufficient to impart stabilization to the carbonylation catalyst. The product stream exits the reactor 20 and is fed via line 2 to a liquid/gas separator 30 and unreacted gas is recycled back via line 3 to carbonylation reactor 20. The product stream is then fed via line 4 to a crude ester distillation column 40 in which the overhead fraction containing methyl acetate and lower boiling materials exits column 40 and is fed via line 13 to a hydrolysis reactor 50. Reactor 50 contains an ester hydrolysis catalyst and is maintained at pre-selected reaction conditions of temperature and pressure, e.g., a temperature from about 50° C. to about 400° C. and a pressure from about 1 to about 10,000 psig, so that a reaction takes place in which the feedstock is converted to a product stream containing acetic acid, methanol, methyl acetate and water. Hydrolysis of methyl acetate in reactor 50 can be carried out as a liquid, gas/liquid, or gas phase reaction with a homogeneous or heterogeneous acidic catalyst. The concentration of carbonylation catalyst and ester hydrolysis catalyst is not narrowly critical and will depend on the desired productivity and other reaction variables. This product stream is fed via line 5 back to crude ester distillation column 40. A side draw (not shown) can optionally be taken from the crude ester distillation column 40 that is rich in methanol and recycled to the carbonylation reactor 20. A bottoms fraction containing acetic acid, methanol and water exits column 40 and is fed via line 6 to an alcohol distillation column 60 in which methanol is removed overhead via line 7 and recycled to carbonylation reactor 20. A bottoms fraction containing acetic acid and water exits column 60 and is fed via line 8 to an extractor column 70. In extractor column 70, the acetic acid is extracted from the tails stream via counter flow extraction with an organic solvent such as diethyl ketone. The diethyl ketone/acetic acid make is fed via line 9 to a solvent recovery column 80 where acetic acid is recovered in the tails stream. The acetic acid can be further refined to desired purity by methods known in the art. A bottoms fraction containing water from extractor column 70 is recycled to hydrolysis reactor 50. An overhead fraction containing solvent and water from solvent recovery column 80 is sent to a condenser unit 90 to give an organic phase and aqueous phase. A portion of the aqueous phase is recycled via line 11 to extractor column 70 and a portion of the organic phase is recycled via line 12 to extractor column 70. Also, a portion of the aqueous phase is recycled via line 16 to solvent recovery column 80 and a portion of the organic phase is recycled via line 15 to solvent recovery column 80. A purge stream may be used to control the buildup of inerts.

The advantages of conducting a process as depicted by FIG. 5 include recycle back to the carbonylation reactor is minimized and thus the size of carbonylation reactor 20 can be reduced, materials of construction of the refining/extraction steps is not exotic and easy control of water in and out of the system. In FIG. 5, methyl acetate recycle back to the carbonylation reactor can be minimized. The optional side draw taken from the crude ester distillation column 40 can eliminate methanol column 60.

Another embodiment of this invention involves a process for converting a feedstock stream comprising at least one of an alcohol and ether and mixtures thereof to a product stream comprising at least one of an ester, acid, acid anhydride and mixtures thereof which comprises (a) feeding at least a portion of a first feedstock stream comprising carbon monoxide and at least a portion of a second feedstock stream comprising an alcohol and/or ether to a carbonylation reaction zone, (b) reacting in said carbonylation reaction zone the carbon monoxide and alcohol and/or ether in the presence of a catalyst comprising a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, or mixtures thereof, under conditions of temperature and pressure sufficient to produce a first crude product stream comprising at least one of an ester, acid, acid anhydride, alcohol, ether, water and mixtures thereof, (c) withdrawing said first crude product stream and unreacted carbon monoxide from said carbonylation reaction zone and feeding at least a portion of the withdrawn stream and carbon monoxide to a liquid/gas separation zone, (d) withdrawing from the liquid/gas separation zone an overhead fraction comprising said carbon monoxide and optionally recycling at least a portion of the withdrawn overhead fraction to said carbonylation reaction zone, (e) withdrawing from the liquid/gas separation zone a bottoms fraction comprising said first crude product stream and feeding at least a portion of the withdrawn bottoms fraction to a hydrolysis/dehydration reaction zone, (f) reacting in the hydrolysis/dehydration reaction zone in the presence of a catalyst comprising an ester hydrolysis catalytic component and an alcohol dehydration catalytic component said first crude product stream under conditions of temperature and pressure sufficient to produce a second crude product stream comprising at least one of an ester, acid, acid anhydride, alcohol, ether, water and mixtures thereof (containing less ester and more acid than said first crude product stream), (g) withdrawing from the hydrolysis/dehydration reaction zone said second crude product stream and feeding at least a portion of the withdrawn stream to a distillation zone, (h) withdrawing from the distillation zone an overhead fraction comprising at least one ether and optionally recycling at least a portion of the withdrawn overhead fraction to said carbonylation reaction zone, (i) withdrawing from the distillation zone a sidedraw fraction comprising at least one of an ester, acid, acid anhydride, alcohol, water and mixtures thereof and optionally recycling at least a portion of the withdrawn sidedraw fraction to said hydrolysis/dehydration reaction zone, and (j) withdrawing from the distillation zone a bottoms fraction comprising said product stream. An ether scrubber zone may be incorporated into this process scheme. For example, at least a portion of the overhead fraction from the liquid/gas separation zone can be fed to an ether scrubber zone. An overhead fraction comprising lower boiling byproducts from the ether scrubber zone can be fed to a feedstock preparation zone and a bottoms fraction comprising a mixture of an alcohol and ether can be fed to the hydrolysis/dehydration reaction zone. Also, in this process scheme, methanol can be fed, in addition to the carbonylation reaction zone, to the hydrolysis/dehydration reaction zone and/or ether scrubber zone. A unique embodiment of this invention involves the coupled hydrolysis/dehydration reaction zone. An illustrative process scheme of this embodiment is set forth in FIG. 6.

Figure 6:
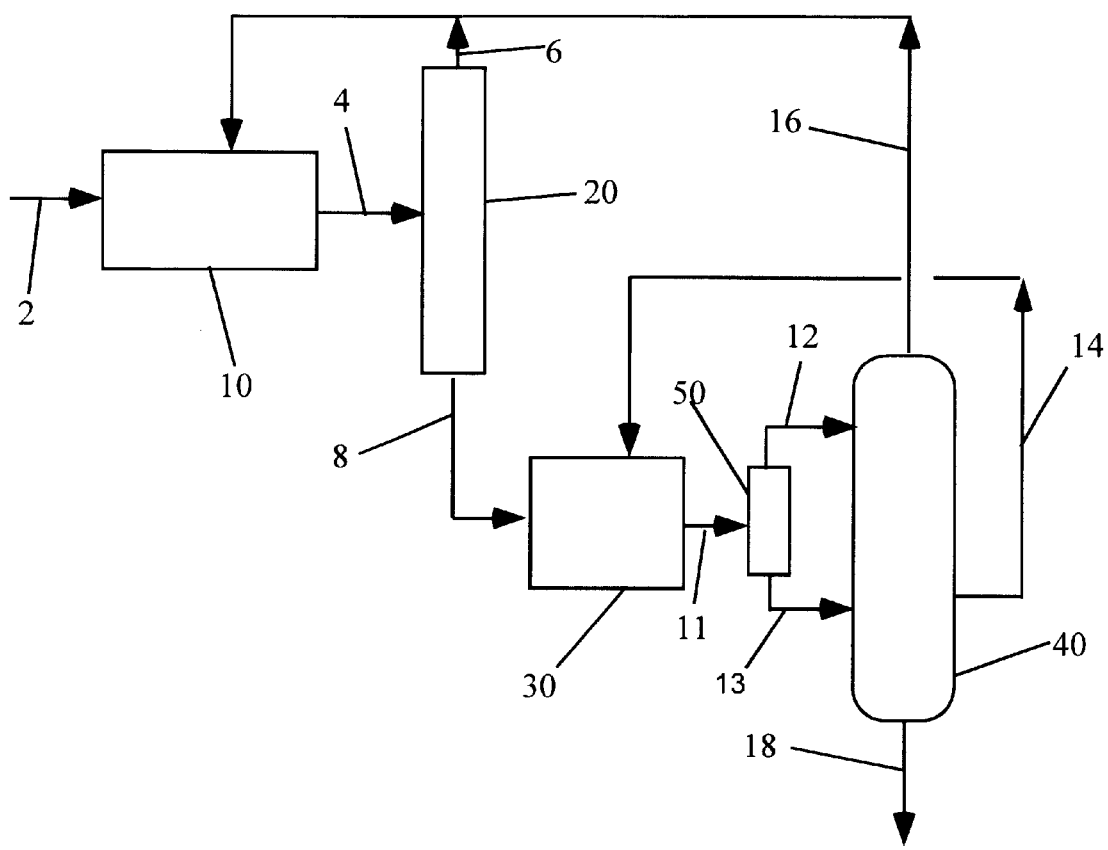
FIG. 6 is a schematic representation of a process flow diagram to make acetic acid from a methanol feedstock and a carbon monoxide-containing feedstock.

In FIG. 6, which is a simplified flow diagram of an embodiment of this invention involving methyl acetate hydrolysis with dimethyl ether removal by distillation and recovery of acetic acid by distillation, a process for the preparation of acetic acid from a carbon monoxide feed stream and methanol and/or dimethyl ether feed stream is shown. Methanol and/or dimethyl ether and carbon monoxide are fed to carbonylation reactor 10 via line 2. In this scheme, methanol and/or dimethyl ether is supplied to the carbonylation reactor 20 from an external source, for example, another process unit or obtained commercially. Methanol and/or dimethyl ether can optionally be formed in situ by feeding synthesis gas to a methanol and/or dimethyl ether producing catalyst that is coupled to the carbonylation catalyst either in the same or different reactors. Likewise, carbon monoxide can optionally be formed in situ by feeding a hydrocarbon stream, e.g., methane and oxygen, to a synthesis gas generation unit which generates a synthesis gas stream. The synthesis gas stream exits the synthesis gas generation unit and is fed to a gas separator in which carbon monoxide is separated from hydrogen. If desired, either methanol, dimethyl ether and/or synthesis gas can be obtained from a different source and fed directly to the carbonylation catalyst. The carbon monoxide stream can have a hydrogen:carbon monoxide molar ratio of from about 20:1 to about 1:20 and a gas hourly space velocity of from about 1 to about 30,000 hour$^{-1}$. The carbonylation reactor 10 contains an alcohol and/or ether carbonylation catalyst and is maintained at pre-selected reaction conditions of temperature and pressure, e.g., a temperature from about 50° C. to about 400° C. and a pressure from about 1 to about 10,000 psig, so that a vapor phase reaction takes place in which the methanol and/or dimethyl ether and carbon monoxide feeds are converted to oxygenates, most preferably containing a large fraction of methyl acetate. The hydrogen partial pressure in carbonylation reactor 10 is sufficient to impart stabilization to the carbonylation catalyst. The product stream exits the reactor 10 and is fed via line 4 to a liquid/gas separator 20 and unreacted gas is recycled back via lines 6 and 16 to carbonylation reactor 10. The product stream containing acetic acid, methyl acetate, methanol, dimethyl ether and water is then fed via line 8 to a hydrolysis/ dehydration reactor 30. Reactor 30 contains an ester hydrolysis catalyst and alcohol dehydration catalyst and is maintained at pre-selected reaction conditions of temperature and pressure, e.g., a temperature from about 50° C. to about 400° C. and a pressure from about 1 to about 10,000 psig, so that a reaction takes place in which the feedstock is converted to a product stream containing acetic acid, dimethyl ether, methanol, methyl acetate and water. Hydrolysis of methyl acetate and dehydration of methanol can be carried out as a liquid, gas/liquid, or gas phase reaction with a homogeneous or heterogeneous acidic catalyst. The concentration of carbonylation catalyst, ester hydrolysis catalyst and alcohol dehydration catalyst is not narrowly critical and will depend on the desired productivity and other reaction variables. The ester hydrolysis catalyst and alcohol dehydration catalyst can be the same or different. The product stream from hydrolysis/dehydration reactor 30 is fed via line 11 to a separator unit 50 to give a dimethyl ether-containing overhead fraction and an acetic acid-containing bottoms fraction. The overhead fraction is fed via line 12 to crude distillation column 40 and the bottoms fraction is fed via line 13 to crude distillation column 40. The crude distillation column 40 is operated at a pressure of from 0 to about 300 psi to keep dimethyl ether liquefied so that it can be pumped via line 16 to the carbonylation reactor 10. Removing dimethyl ether allows for high conversion of methyl acetate to acetic acid. An overhead fraction containing dimethyl ether from crude distillation column 40 is recycled via line 16 to carbonylation reactor 10 and/or to a synthesis gas generation unit (not shown). A side draw line 14 is taken from the crude distillation column 40 that is rich in methyl acetate, methanol and water and line 14 is sent to the hydrolysis/dehydration reactor 30. A bottoms fraction containing acetic acid from crude distillation column 40 exits via line 18. The bottoms fraction can be further refined by known methods depending on the desired acetic acid purity. A purge stream may be used to control the buildup of inerts.

The advantages of conducting a process as depicted by FIG. 6 include it being a simple configuration utilizing a hydrolysis/dehydration reactor to convert methyl acetate to acetic acid and methanol to dimethyl ether. In FIG. 6, methyl acetate recycle to the carbonylation reactor is minimized.

Another embodiment of this invention involves a process for converting a feedstock stream comprising at least one of an alcohol and ether and mixtures thereof to a product stream comprising at least one of an ester, acid, acid anhydride and mixtures thereof which comprises (a) feeding at least a portion of a first feedstock stream comprising carbon monoxide to a carbonylation reaction zone, (b) feeding at least a portion of a second feedstock stream comprising an alcohol and/or ether to a hydrolysis/ dehydration reaction zone, (c) reacting in a carbonylation reaction zone the carbon monoxide stream and an ether-rich stream from an ether separation zone in the presence of a catalyst comprising a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, or mixtures thereof, under conditions of temperature and pressure sufficient to produce a first crude product stream comprising at least one of an ester, acid, acid anhydride, alcohol, ether, water and mixtures thereof, (d) withdrawing said first crude product stream and unreacted carbon monoxide from said carbonylation reaction zone and feeding at least a portion of the withdrawn stream and carbon monoxide to a liquid/gas separation zone, (e) withdrawing from the liquid/gas separation zone an overhead fraction comprising said carbon monoxide and optionally recycling at least a portion of the withdrawn overhead fraction to said carbonylation reaction zone, (f) withdrawing from the liquid/gas separation zone a bottoms fraction comprising said first crude product stream and feeding at least a portion of the withdrawn bottoms fraction to said hydrolysis/dehydration reaction zone, (g) reacting in the hydrolysis/dehydration reaction zone in the presence of a catalyst comprising an ester hydrolysis catalytic component and an alcohol dehydration catalytic component said withdrawn bottoms fraction comprising a mixture of an alcohol and ether under conditions of temperature and pressure sufficient to produce a second crude product stream comprising at least one of an ester, acid, acid anhydride, alcohol, ether, water and mixtures thereof (containing less ester and more acid than said first crude product stream), (h) withdrawing from the hydrolysis/dehydration reaction zone said second crude product stream and feeding at least a portion of the withdrawn stream to said ether separation zone to provide an overhead fraction comprising said ether-rich stream and a bottoms fraction comprising at least one of an ester, acid, acid anhydride, alcohol, water and mixtures thereof, (i) withdrawing from the ether separation zone said overhead fraction and optionally recycling at least a portion of the withdrawn overhead fraction to said carbonylation reaction zone, (j) withdrawing from the ether separation zone said bottoms fraction and feeding at least a portion of the withdrawn bottoms fraction to a distillation zone, (k) withdrawing from the distillation zone an overhead fraction comprising a mixture of an alcohol, ester and ether and feeding at least a portion of the withdrawn overhead fraction to said hydrolysis/dehydration reaction zone, and (l) withdrawing from the distillation zone a bottoms fraction comprising said product stream. An ether scrubber zone may be incorporated into this process scheme. For example, at least a portion of the overhead fraction from the liquid/gas separation zone can be fed to an ether scrubber zone. An overhead fraction comprising lower boiling byproducts from the ether scrubber zone can be fed to a feedstock preparation zone and a bottoms fraction comprising a mixture of an alcohol and ether can be fed to the hydrolysis/dehydration reaction zone. Also, in this process scheme, methanol can be fed, in addition to the hydrolysis/dehydration reaction zone, to the carbonylation reaction zone and/or ether scrubber zone. A unique embodiment of this invention involves the coupled hydrolysis/dehydration reaction zone. An illustrative process scheme of this embodiment is set forth in FIG. 7.

Figure 7:
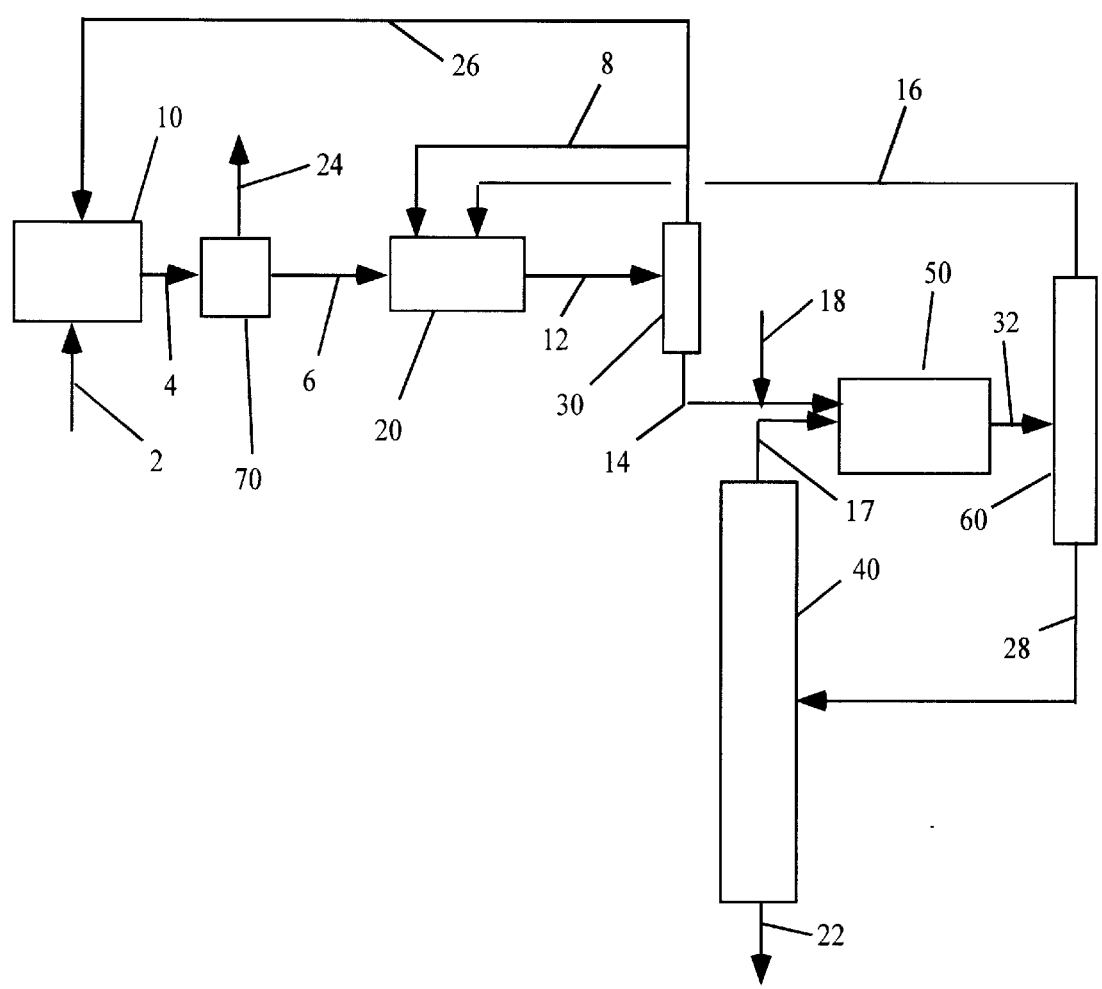
FIG. 7 is a schematic representation of a process flow diagram to make acetic acid from a methanol feedstock and a carbon monoxide-containing feedstock.

In FIG. 7, which is a simplified flow diagram of an embodiment of this invention involving a coupled hydrolysis/dehydration reaction zone, a process for the preparation of acetic acid from a synthesis gas feed stream and methanol feed stream is shown. A hydrocarbon stream, e.g., methane and oxygen, is supplied via line 2 to a synthesis gas generation unit 10 which generates a synthesis gas stream. The synthesis gas stream can have a hydrogen-:carbon monoxide molar ratio of from about 20:1 to about 1:20 and a gas hourly space velocity of from about 1 to about 30,000 hour$^{-1}$. The synthesis gas stream exits the synthesis gas generation unit 10 and is fed via line 4 to a gas separator 70 in which carbon monoxide is separated from hydrogen. Hydrogen is removed via line 24 and a carbon monoxide-rich stream (carbon monoxide:hydrogen molar ratio of greater than about 1:1 to about 1000:1) is fed via line 6 to carbonylation reactor 20. The removal of hydrogen limits the amount of hydrogen entering the carbonylation reactor 20 and thus helps to improve selectivity by reducing hydrocarbon formation. However, as described herein, the carbonylation reaction is preferably conducted in the presence of a stabilizing amount of hydrogen, i.e., an amount sufficient to impart stabilization to the carbonylation catalyst. A dimethyl ether-rich stream is fed to carbonylation reactor 20 from the hydrolysis/dehydration reactor 50 and ether stripper column 60 as described below. The carbonylation reactor 20 contains a carbonylation catalyst and is maintained at pre-selected reaction conditions of temperature and pressure, e.g., a temperature from about 50° C. to about 400° C. and a pressure from about 1 to about 10,000 psig, so that a vapor phase reaction takes place in which the dimethyl ether and/or methanol and carbon monoxide feeds are converted to oxygenates, most preferably containing a large fraction of methyl acetate. The concentration of carbonylation catalyst, ester hydrolysis catalyst and alcohol dehydration catalyst is not narrowly critical and will depend on the desired productivity and other reaction variables. The ester hydrolysis catalyst and alcohol dehydration catalyst can be the same or different. The hydrogen partial pressure in carbonylation reactor 20 is sufficient to impart stabilization to the carbonylation catalyst. The product stream exits the reactor 20 and is fed via line 12 to a liquid/gas separator 30 and unreacted gas is recycled back via lines 26 and 8 to carbonylation reactor 20 and/or via line 26 to synthesis gas generation unit 10. The bottoms fraction from the liquid/gas separator 30 containing acetic acid, methyl acetate, methanol, dimethyl ether and water is then fed via line 14 to hydrolysis/dehydration reactor 50. Methanol and/or dimethyl ether and optionally water are fed via line 18 by way of line 14 to the hydrolysis/dehydration reactor 50. In this scheme, methanol and/or dimethyl ether is supplied to the hydrolysis/dehydration reactor 50 from an external source, for example, another process unit or obtained commercially. Methanol and/or dimethyl ether can optionally be formed in situ by feeding synthesis gas to a methanol and/or dimethyl ether producing catalyst. If desired, either methanol, dimethyl ether and/or synthesis gas can be obtained from a different source and the methanol and/or dimethyl ether fed directly to the hydrolysis/dehydration reactor 50 and the synthesis gas (carbon monoxide) fed directly to the carbonylation catalyst. Reactor 50 contains an ester hydrolysis catalyst and alcohol dehydration catalyst and is maintained at pre-selected reaction conditions of temperature and pressure, e.g., a temperature from about 50° C. to about 400° C. and a pressure from about 1 to about 10,000 psig, so that a reaction takes place in which the feedstock is converted to a product stream containing acetic acid, dimethyl ether, methanol, methyl acetate and water. The product stream exits the hydrolysis/dehydration reactor 50 and is sent to an ether stripper column 60 via line 32. In ether stripper column 60, dimethyl ether is removed overhead via line 16 and is fed to carbonylation reactor 20, and a bottoms fraction containing methyl acetate, methanol, acetic acid and water is fed via line 28 to a refining column 40. An overhead fraction containing methyl acetate, methanol and water from refining column 40 is sent via line 17 to the hydrolysis/dehydration reactor 50. A bottoms fraction containing acetic acid from refining column 40 exits via line 22. The acetic acid can be further refined to desired purity by methods known in the art. A purge stream may be used to control the buildup of inerts.

The advantages of conducting a process as depicted by FIG. 7 include reducing the total flow through the carbonylation reactor, the methyl acetate hydrolysis reaction is shifted toward acetic acid by coupling the dehydration and hydrolysis steps, minimizing the size of the recycle stream back to the carbonylation reactor, the hydrolysis/dehydration is conducted in the absence of carbon monoxide which maximizes the rate by avoiding dilution with carbon monoxide. In FIG. 7, methyl acetate recycle to the carbonylation reactor is minimized.

Another embodiment of this invention involves a process for converting a feedstock stream comprising at least one of an alcohol and ether and mixtures thereof to a product stream comprising at least one of an ester, acid, acid anhydride and mixtures thereof which comprises (a) feeding at least a portion of a first feedstock stream comprising carbon monoxide to a carbonylation reaction zone, (b) feeding at least a portion of a second feedstock stream comprising an alcohol and/or ether to a reactive distillation zone, (c) reacting in said carbonylation reaction zone the carbon monoxide stream and an ether-containing stream from said reactive distillation zone in the presence of a catalyst comprising a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, or mixtures thereof, under conditions of temperature and pressure sufficient to produce a crude product stream comprising at least one of an ester, acid, acid anhydride, alcohol, ether, water and mixtures thereof, (d) withdrawing said crude product stream and unreacted carbon monoxide from said carbonylation reaction zone and feeding at least a portion of the withdrawn stream and carbon monoxide to a liquid/gas separation zone, (e) withdrawing from the liquid/gas separation zone an overhead fraction comprising said carbon monoxide and lower boiling byproducts and optionally feeding at least a portion of the withdrawn overhead fraction to a feedstock preparation zone and/or said carbonylation reaction zone, (f) withdrawing from the liquid/gas separation zone a bottoms fraction comprising at least one of an ester, acid, ether, alcohol, water and mixtures thereof and feeding at least a portion of the withdrawn bottoms fraction to said reactive distillation zone, said reactive distillation zone containing a catalyst comprising an ester hydrolysis catalytic component and an alcohol dehydration catalytic component, (g) withdrawing from the reactive distillation zone an overhead fraction comprising said ether-containing stream and feeding at least a portion of the ether-containing stream to said carbonylation reaction zone, and (h) withdrawing from the reactive distillation zone a bottoms fraction comprising said product stream. An ether scrubber zone may be incorporated into this process scheme. For example, at least a portion of the overhead fraction from the liquid/gas separation zone can be fed to an ether scrubber zone. An overhead fraction comprising lower boiling byproducts from the ether scrubber zone can be fed to a feedstock preparation zone and a sidedraw fraction comprising a mixture of an alcohol and ether can be fed to the reactive distillation zone. In this process scheme, methanol can be fed to the carbonylation reaction zone, reactive distillation zone and/or ether scrubber zone (if present). A unique embodiment of this invention involves the reactive distillation zone having coupled ester hydrolysis and alcohol dehydration. An illustrative process scheme of this embodiment is set forth in FIG. 8.

Figure 8:
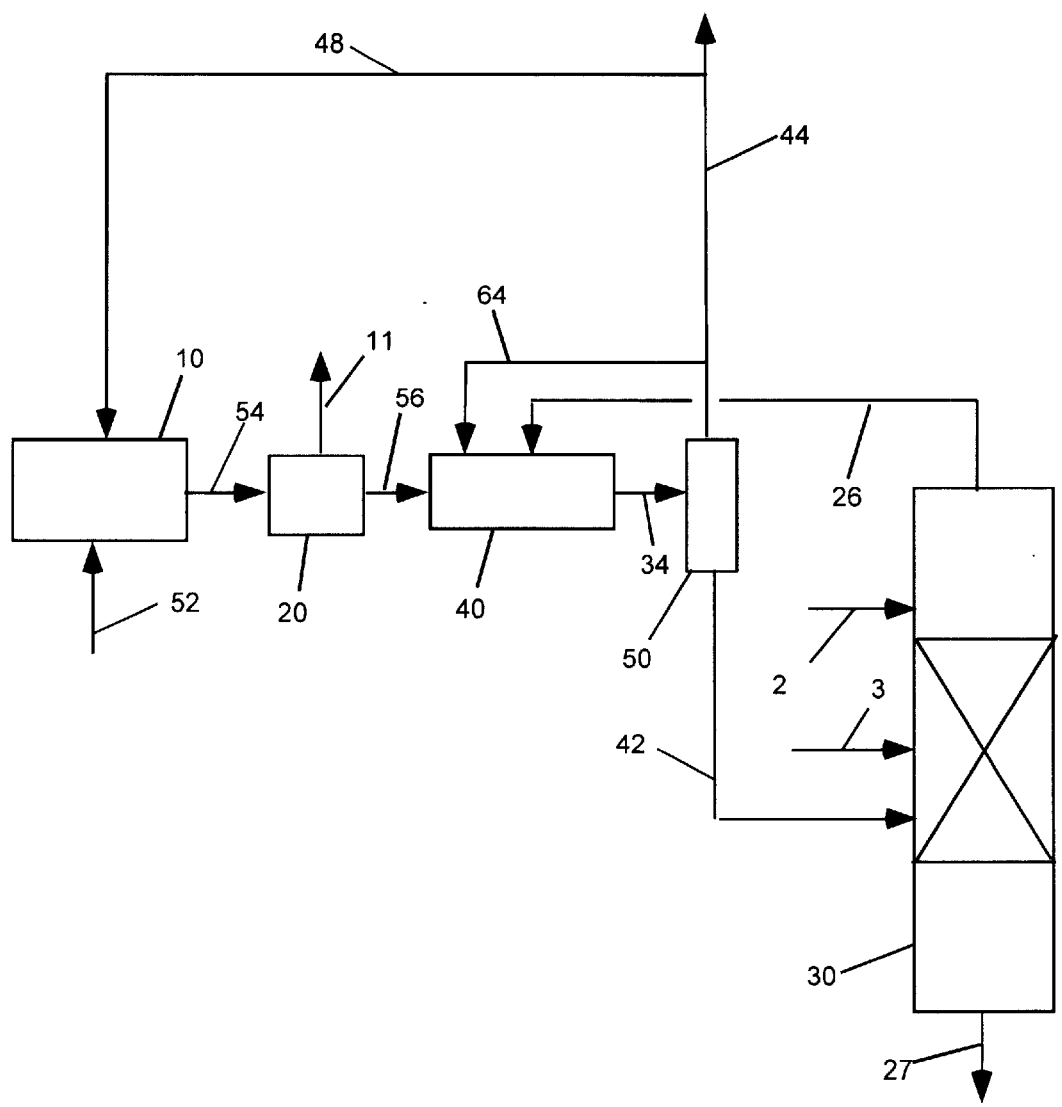
FIG. 8 is a schematic representation of a process flow diagram using reactive distillation to make acetic acid from a methanol feedstock and a feedstock gaseous mixture comprising carbon monoxide and hydrogen gases prepared from a hydrocarbon feed to a synthesis gas generation unit.

In FIG. 8, which is a simplified flow diagram of an embodiment of this invention involving recovery of acetic acid by reactive distillation, a process for the preparation of acetic acid from a carbon monoxide feed stream and methanol and/or dimethyl ether feed stream is shown. A hydrocarbon stream, e.g., methane and oxygen, is supplied via line 52 to a synthesis gas generation unit 10 which generates a synthesis gas stream. The synthesis gas stream can have a hydrogen:carbon monoxide molar ratio of from about 20:1 to about 1:20 and a gas hourly space velocity of from about 1 to about 30,000 hour$^{-1}$. The synthesis gas stream exits the synthesis gas generation unit 10 and is fed via line 54 to a gas separator 20 in which carbon monoxide is separated from hydrogen. Hydrogen is removed via line 11 and a carbon monoxide-rich stream (carbon monoxide:hydrogen molar ratio of greater than about 1:1 to about 1000:1) is fed via line 56 to carbonylation reactor 40. The removal of hydrogen limits the amount of hydrogen entering the carbonylation reactor 40 and thus helps to improve selectivity by reducing hydrocarbon formation. However, as described herein, the carbonylation reaction is preferably conducted in the presence of a stabilizing amount of hydrogen, i.e., an amount sufficient to impart stabilization to the carbonylation catalyst. Methanol and/or dimethyl ether is fed via line 2 to reactive distillation column 30 just above the reaction zone. Water is optionally fed via line 3 to the reactive distillation column 30 to increase the conversion of methyl acetate to acetic acid. In this scheme, methanol and/or dimethyl ether is supplied to the reactive distillation column 30 from an external source, for example, another process unit or obtained commercially. Methanol and/or dimethyl ether can optionally be formed in situ by feeding synthesis gas to a methanol and/or dimethyl ether producing catalyst that is coupled to the reactive distillation column 30. If desired, either methanol, dimethyl ether and/or synthesis gas can be obtained from a different source and the methanol and/or dimethyl ether fed directly to reactive distillation column 30 and the synthesis gas (carbon monoxide) fed directly to the carbonylation catalyst. Reactive distillation column 30 contains an ester hydrolysis catalyst and alcohol dehydration catalyst and is maintained at pre-selected reaction conditions of temperature, e.g., a temperature from about 50° C. to about 350° C. and a pressure from about 0 to about 300 psig, so that a reaction takes place in which the feedstock is converted to an overhead fraction containing dimethyl ether and a bottoms fraction containing acetic acid. The overhead fraction exits the reactive distillation column 30 and is sent to a carbonylation reactor 40 via line 26. In this scheme, very little methanol goes to the carbonylation reactor 40. The carbonylation reactor 40 contains an alcohol and/or ether carbonylation catalyst and is maintained at pre-selected reaction conditions of temperature and pressure, e.g., a temperature from about 50° C. to about 400° C. and a pressure from about 1 to about 10,000 psig, so that a vapor phase reaction takes place in which the dimethyl ether and/or methanol and carbon monoxide feeds are converted to oxygenates, most preferably containing a large fraction of methyl acetate. The concentration of carbonylation catalyst, ester hydrolysis catalyst and alcohol dehydration catalyst is not narrowly critical and will depend on the desired productivity and other reaction variables. The ester hydrolysis catalyst and alcohol dehydration catalyst can be the same or different. The hydrogen partial pressure in carbonylation reactor 40 is sufficient to impart stabilization to the carbonylation catalyst. The product stream exits the reactor 40 and is fed via line 34 to a liquid/gas separator 50 and unreacted gas is recycled back via lines 44 and 64 to carbonylation reactor 40. A portion of the lights stream from liquid/gas separator 50 containing carbon monoxide, dimethyl ether and hydrocarbons is removed overhead and sent via lines 44 and 48 to synthesis gas generation unit 10. The bottoms fraction from the liquid/gas separator 50 containing methyl acetate, acetic acid, methanol, dimethyl ether and water is then fed via line 42 to the lower portion of reactive distillation column 30 with most or all of the reaction occurring above the lower feed stage. A dehydration unit (not shown) optionally may be located prior to the reactive distillation column 30 to dehydrate the methanol in stream 42. A bottoms fraction containing acetic acid from reactive distillation column 30 exits via line 27. The stages below the reactive section of reactive distillation column 30 purify acetic acid and the stages above the reactive section purify dimethyl ether. The acetic acid can be further refined to desired purity by methods known in the art. A purge stream may be used to control the buildup of inerts.

The advantages of conducting a process as depicted by FIG. 8 include the hydrolysis of methyl acetate, dehydration of methanol and recovery of acetic acid being carried out in a single reactive distillation column which allows the hydrolysis reaction to proceed to completion, a very simplified process, low capital, improved control of the process, and small recycle streams.

Another embodiment of this invention involves a process for converting a feedstock stream comprising at least one of an alcohol and ether and mixtures thereof to a product stream comprising at least one of an ester, acid, acid anhydride and mixtures thereof which comprises (a) feeding at least a portion of a first feedstock stream comprising carbon monoxide to a carbonylation reaction zone, (b) feeding at least a portion of a second feedstock stream comprising an alcohol and optionally an ether to a dehydration reactive distillation zone, (c) reacting in said carbonylation reaction zone the carbon monoxide and an ether-containing stream from said dehydration reactive distillation zone in the presence of a catalyst comprising a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, or mixtures thereof, under conditions of temperature and pressure sufficient to produce a crude product stream comprising at least one of an ester, acid, acid anhydride, alcohol, ether, water and mixtures thereof, (d) withdrawing said crude product stream and unreacted carbon monoxide from said carbonylation reaction zone and feeding at least a portion of the withdrawn stream and carbon monoxide to a liquid/gas separation zone, (e) withdrawing from the liquid/gas separation zone an overhead fraction comprising said carbon monoxide and optionally recycling at least a portion of the withdrawn overhead fraction to said carbonylation reaction zone, (f) withdrawing from the liquid/gas separation zone a bottoms fraction comprising said crude product stream and feeding at least a portion of the withdrawn bottoms fraction to a hydrolysis reactive distillation zone, said hydrolysis reactive distillation zone containing an ester hydrolysis catalyst, (g) withdrawing from the hydrolysis reactive distillation zone an overhead fraction comprising a mixture of an alcohol, ether and ester and feeding at least a portion of the withdrawn overhead fraction to said dehydration reactive distillation zone, said dehydration reactive distillation zone containing an alcohol dehydration catalyst, (h) withdrawing from the dehydration reactive distillation zone an overhead fraction comprising said ether-containing stream and feeding at least a portion of the ether-containing stream to said carbonylation reaction zone, (i) withdrawing from the dehydration reactive distillation zone a bottoms fraction comprising at least one of an acid, ester and water and feeding at least a portion of the withdrawn bottoms fraction to said hydrolysis reactive distillation zone, and G) withdrawing from the hydrolysis reactive distillation zone a bottoms fraction comprising said product stream. An ether scrubber zone may be incorporated into this process scheme. For example, at least a portion of the overhead fraction from the liquid/gas separation zone can be fed to an ether scrubber zone. An overhead fraction comprising lower boiling byproducts from the ether scrubber zone can be fed to a feedstock preparation zone and a bottoms fraction comprising a mixture of an alcohol and ether can be fed to the dehydration reactive distillation reaction zone. Also, in this process scheme, methanol can be fed, in addition to the dehydration reactive distillation zone, to the carbonylation reaction zone and/or ether scrubber zone. A unique embodiment of this invention involves the reactive distillation zone having decoupled ester hydrolysis and alcohol dehydration. An illustrative process scheme of this embodiment is set forth in FIG. 9.

Figure 9:
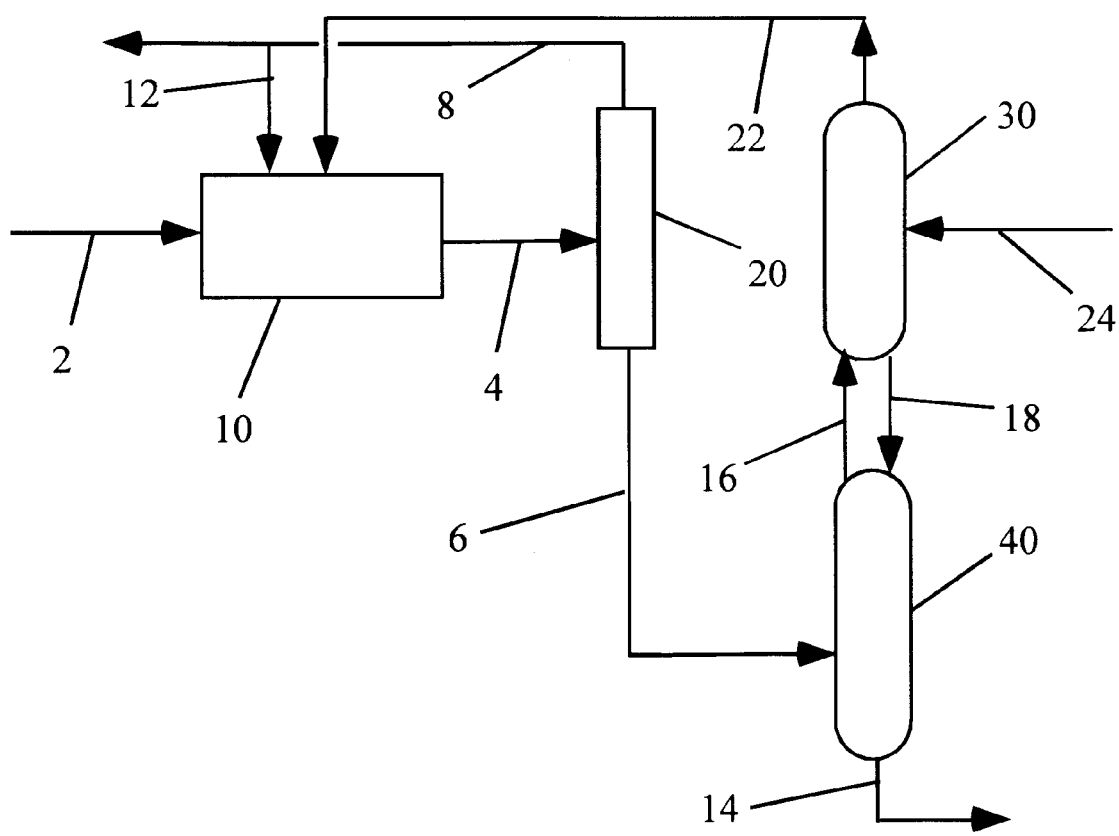
FIG. 9 is a schematic representation of a process flow diagram using decoupled reactive distillation to make acetic acid from a methanol feedstock and a carbon monoxide-containing feedstock.

In FIG. 9, which is a simplified flow diagram of an embodiment of this invention involving decoupled reactive distillation with methanol feed to the dehydration column, a process for the preparation of acetic acid from a carbon monoxide feed stream and methanol feed stream is shown. A synthesis gas generation unit (not shown) generates the required carbon monoxide containing a small amount of hydrogen which is fed to the carbonylation reactor 10 along with a dimethyl ether rich stream from the dehydration reactive distillation column 30 as described below. The synthesis gas stream can have a hydrogen:carbon monoxide molar ratio of from about 20:1 to about 1:20 and a gas hourly space velocity of from about 1 to about 30,000 hour$^{-1}$. Carbon monoxide is fed to carbonylation reactor 10 via line 2. Methanol and optionally dimethyl ether is fed via line 24 to dehydration reactive distillation column 30. Methanol and/or dimethyl ether can optionally be formed in situ by feeding synthesis gas to a methanol and/or dimethyl ether producing catalyst that is coupled to the dehydration reactive distillation catalyst either in the same or different reactors. The synthesis gas stream exits the synthesis gas generation unit and is fed to a gas separator in which carbon monoxide is separated from hydrogen. If desired, either methanol, synthesis gas or both can be obtained from a different source and the methanol fed directly to dehydration reactive distillation column 30 and the synthesis gas (carbon monoxide) fed directly to the carbonylation catalyst. Dehydration reactive distillation column 30 contains an alcohol dehydration catalyst and is maintained at pre-selected reaction conditions of temperature and pressure, e.g., a temperature from about 50° C. to about 400° C. and a pressure from about 0 to about 300 psig, so that a reaction takes place in which the feedstock is converted to an overhead fraction containing dimethyl ether and a bottoms fraction containing water. The overhead fraction exits the dehydration reactive distillation column 30 and is sent to carbonylation reactor 10 via lines 22 and 12. In this scheme, very little methanol goes to the carbonylation reactor 10. The bottoms fraction from dehydration reactive distillation column 30 is sent via line 18 to a hydrolysis reactive distillation column 40. The carbonylation reactor 10 contains an alcohol and/or ether carbonylation catalyst and is maintained at pre-selected reaction conditions of temperature and pressure, e.g., a temperature from about 50° C. to about 400° C. and a pressure from about 1 to about 10,000 psig, so that a vapor phase reaction takes place in which the dimethyl ether and/or methanol and carbon monoxide feeds are converted to oxygenates, most preferably containing a large fraction of methyl acetate. The hydrogen partial pressure in carbonylation reactor 10 is sufficient to impart stabilization to the carbonylation catalyst. The product stream exits the reactor 10 and is fed via line 4 to a liquid/gas separator 20 and unreacted gas is recycled back via lines 8 and 12 to carbonylation reactor 10 and hydrocarbons recycled back to a synthesis gas generation unit. The bottoms fraction from the liquid/gas separator 20 containing acetic acid, methyl acetate, methanol, dimethyl ether and water is then fed via line 6 to the hydrolysis reactive distillation column 40. Hydrolysis reactive distillation column 40 contains an ester hydrolysis catalyst and is maintained at pre-selected reaction conditions of temperature and pressure, e.g., a temperature from about 50° C. to about 400° C. and a pressure from about 0 to about 300 psig, so that a reaction takes place in which the feedstock is converted to an overhead fraction containing methanol and water and a bottoms fraction containing acetic acid. The concentration of carbonylation catalyst, ester hydrolysis catalyst and alcohol dehydration catalyst is not narrowly critical and will depend on the desired productivity and other reaction variables. The ester hydrolysis catalyst and alcohol dehydration catalyst can be the same or different. An overhead fraction containing methanol and water from hydrolysis reactive distillation column 40 is fed via line 16 to the dehydration reactive distillation column 30. A bottoms fraction containing acetic acid from the hydrolysis reactive distillation column 40 exits via line 14. The acetic acid can be further refined to desired purity by methods known in the art. A purge stream may be used to control the buildup of inerts.

The advantages of conducting a process as depicted by FIG. 9 include the separate stages of the reactive distillation, i.e., the hydrolysis reactive distillation and dehydration reactive distillation, can be controlled independently, the materials of construction of the split reactive distillation columns can both be stainless steel, and have separate operating control of the dehydration reactive distillation column 30 and hydrolysis reactive distillation column 40 (both run at different temperatures/pressures).

Alternatively, the process depicted in FIG. 9 may be conducted in a scheme involving decoupled reactive distillation with methanol feed to the carbonylation reactor. Such a scheme may be operated in a manner similar to FIG. 9 with the exception that the methanol is fed to the carbonylation reactor.

The advantages of conducting such an alternative process include the separate stages of the reactive distillation can be controlled independently, the materials of construction of the split reactive distillation columns can both be stainless steel, allows dimethyl ether to be formed in the reactor and can reduce the size of the dehydration reactive distillation column, and have separate operating control of the dehydration reactive distillation column and hydrolysis reactive distillation column (both run at different temperatures/pressures).

Another embodiment of this invention involves a process for converting a feedstock stream comprising at least one of an alcohol and ether and mixtures thereof to a product stream comprising at least one of an ester, acid, acid anhydride and mixtures thereof which comprises (a) feeding at least a portion of a first feedstock stream comprising carbon monoxide to a carbonylation reaction zone, (b)

feeding at least a portion of a second feedstock stream comprising an alcohol and/or ether to a hydrolysis/dehydration reaction zone, (c) reacting in a carbonylation reaction zone the carbon monoxide stream and an ether-rich stream from an ether separation zone in the presence of a catalyst comprising a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, or mixtures thereof, under conditions of temperature and pressure sufficient to produce a first crude product stream comprising at least one of an ester, acid, acid anhydride, alcohol, ether, water and mixtures thereof, (d) withdrawing said first crude product stream and unreacted carbon monoxide from said carbonylation reaction zone and feeding at least a portion of the withdrawn stream and carbon monoxide to a first lights separation zone, (e) withdrawing from the first lights separation zone an overhead fraction comprising said carbon monoxide and optionally recycling at least a portion of the withdrawn overhead fraction to said carbonylation reaction zone, (f) withdrawing from the first lights separation zone a bottoms fraction comprising said first crude product stream and feeding at least a portion of the withdrawn bottoms fraction to a liquid/gas separation zone, (g) withdrawing from the liquid/gas separation zone an overhead fraction comprising said carbon monoxide and optionally recycling at least a portion of the withdrawn overhead fraction to said carbonylation reaction zone, (h) withdrawing from the liquid/gas separation zone a bottoms fraction comprising said first crude product stream and feeding at least a portion of the withdrawn bottoms fraction to said hydrolysis/dehydration reaction zone, (i) reacting in the hydrolysis/dehydration reaction zone in the presence of a catalyst comprising an ester hydrolysis catalytic component and an alcohol dehydration catalytic component said withdrawn bottoms fraction comprising a mixture of an alcohol and ether under conditions of temperature and pressure sufficient to produce a second crude product stream comprising at least one of an ester, acid, acid anhydride, alcohol, ether, water and mixtures thereof (containing less ester and more acid than said first crude product stream), (j) withdrawing from the hydrolysis/dehydration reaction zone said second crude product stream and feeding at least a portion of the withdrawn stream to a second lights separation zone, (k) withdrawing from the second lights separation zone an overhead fraction comprising at least one of an ether, ester, acid, acid anhydride, alcohol, water and mixtures thereof and feeding at least a portion of the withdrawn overhead fraction to an ether separation zone, (l) withdrawing from the ether separation zone an overhead fraction comprising an ether-rich stream and optionally recycling at least a portion of the withdrawn overhead fraction to said carbonylation reaction zone, (m) withdrawing from the ether separation zone a bottoms fraction comprising at least one of an ester, acid, acid anhydride, alcohol, ether, water and mixtures thereof and and optionally recycling at least a portion of the withdrawn bottoms fraction to said hydrolysis/dehydration reaction zone, (n) withdrawing from the second lights separation zone a bottoms fraction comprising at least one of an acid, ether, ester, acid anhydride, alcohol, water and mixtures thereof and feeding at least a portion of the withdrawn bottoms fraction to an acid separation zone, (o) withdrawing from the acid separation zone an overhead fraction comprising at least one of an ether, ester, acid anhydride, alcohol, acid, water and mixtures thereof and optionally recycling at least a portion of the withdrawn overhead fraction to said hydrolysis/dehydration reaction zone, and (p) withdrawing from the acid separation zone a bottoms fraction comprising said product stream. In this process scheme, methanol can be fed, in addition to the hydrolysis/dehydration reaction zone, to the carbonylation reaction zone. A unique embodiment of this invention involves the coupled hydrolysis/dehydration reaction zone. An illustrative process scheme of this embodiment is set forth in FIG. 10.

Figure 10:
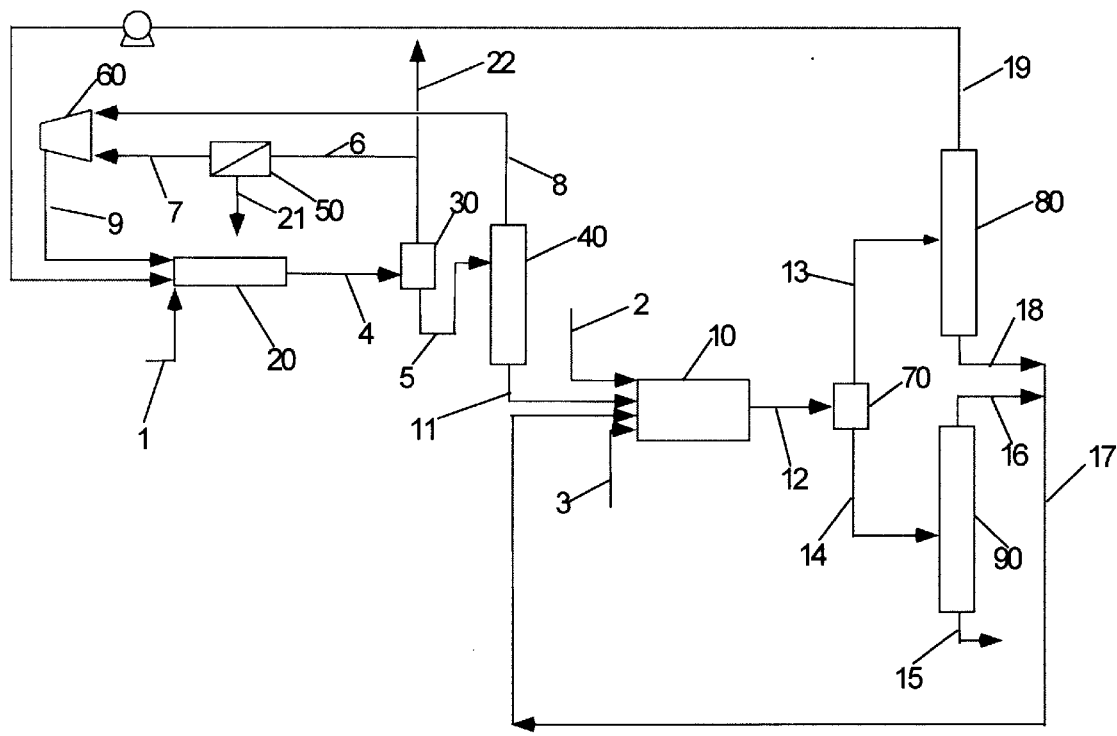
FIG. 10 is a schematic representation of a process flow diagram to make acetic acid from a methanol feedstock and a carbon monoxide-containing feedstock.

In FIG. 10, which is a simplified flow diagram of an embodiment of this invention involving a coupled hydrolysis/dehydration reaction zone, a process for the preparation of acetic acid from a synthesis gas feed stream and methanol feed stream is shown. A hydrocarbon stream, e.g., methane and oxygen, is supplied to a synthesis gas generation unit (not shown) which generates a synthesis gas stream. The synthesis gas stream can have a hydrogen:carbon monoxide molar ratio of from about 20:1 to about 1:20 and a gas hourly space velocity of from about 1 to about 30,000 hour$^{-1}$. The synthesis gas stream exits the synthesis gas generation unit and is fed to a gas separator (not shown) in which carbon monoxide is separated from hydrogen. Hydrogen is removed and a carbon monoxide-rich stream (carbon monoxide:hydrogen molar ratio of greater than about 1:1 to about 1000:1) is fed via line 1 to carbonylation reactor 20. The removal of hydrogen limits the amount of hydrogen entering the carbonylation reactor 20 and thus helps to improve selectivity by reducing hydrocarbon formation. However, as described herein, the carbonylation reaction is preferably conducted in the presence of a stabilizing amount of hydrogen, i.e., an amount sufficient to impart stabilization to the carbonylation catalyst. A dimethyl ether-rich stream is fed to carbonylation reactor 20 from the hydrolysis/dehydration reactor 10 and ether distillation column 80 as described below. The carbonylation reactor 20 contains a carbonylation catalyst and is maintained at preselected reaction conditions of temperature and pressure, e.g., a temperature from about 50° C. to about 400° C. and a pressure from about 1 to about 10,000 psig, so that a vapor phase reaction takes place in which the dimethyl ether and/or methanol and carbon monoxide feeds are converted to oxygenates, most preferably containing a large fraction of methyl acetate. The concentration of carbonylation catalyst, ester hydrolysis catalyst and alcohol dehydration catalyst is not narrowly critical and will depend on the desired productivity and other reaction variables. The ester hydrolysis catalyst and alcohol dehydration catalyst can be the same or different. The hydrogen partial pressure in carbonylation reactor 20 is sufficient to impart stabilization to the carbonylation catalyst. The product stream exits the reactor 20 and is fed via line 4 to a flash tank 30 where unreacted gas is recycled back via lines 6, 7 and 9 to carbonylation reactor 20. A purge stream 22 may be used to control the buildup of inerts. The recycled gas may flow through a membrane separator 50 in which hydrogen is removed via line 21. The recycled gas may also flow through compressor 60 to attain a pressure of about 1000 psi prior to entering carbonylation reactor 20. The bottoms fraction from flash tank 30 containing methyl acetate, dimethyl ether and unreacted gases is then fed via line 5 to liquid/gas separator 40 and unreacted gases are recycled back via lines 8 and 9 to carbonylation reactor 20. The bottoms fraction from the liquid/gas separator 30 containing methyl acetate and dimethyl ether is then fed via line 11 to hydrolysis/dehydration reactor 10. Methanol and/or dimethyl ether is fed via line 2 to the hydrolysis/dehydration reactor 10. In this scheme, methanol and/or dimethyl ether is supplied to the hydrolysis/dehydration reactor 10 from an external source, for example, another process unit or obtained commercially. Methanol and/or dimethyl ether can optionally be formed in situ by feeding synthesis gas to a methanol and/or dimethyl ether producing catalyst. If desired, either methanol, dimethyl ether and/or synthesis gas can be obtained from a different source and the methanol and/or dimethyl ether fed directly to the hydrolysis/dehydration reactor 10 and the synthesis gas (carbon monoxide) fed directly to the carbonylation catalyst. Reactor 10 contains an ester hydrolysis catalyst and alcohol dehydration catalyst and is maintained at pre-selected reaction conditions of temperature and pressure, e.g., a temperature from about 50° C. to about 400° C. and a pressure from about 1 to about 10,000 psig, so that a reaction takes place in which the feedstock is converted to a product stream containing acetic acid, dimethyl ether, methanol, methyl acetate and water. The product stream exits the hydrolysis/dehydration reactor 10 and is sent to flash tank 70 via line 12. In flash tank 70, dimethyl ether, methyl acetate and water are removed overhead via line 13 and is fed to ether distillation column 80, and a bottoms fraction containing acetic acid, methyl acetate, methanol and water is fed via line 14 to acid distillation column 90. In ether distillation column 80, dimethyl ether is removed overhead via line 19 and is fed to carbonylation reactor 20, and a bottoms fraction containing methyl acetate, methanol, acetic acid and water is recycled via lines 18 and 17 to hydrolysis/dehydration reactor 10. An overhead fraction containing methyl acetate, methanol and water from acid distillation column 90 is recycled via lines 16 and 17 to the hydrolysis/dehydration reactor 10. A bottoms fraction containing acetic acid from acid distillation column 90 exits via line 15. The acetic acid can be further refined to desired purity by methods known in the art.

The advantages of conducting a process as depicted by FIG. 10 include reducing the total flow through the carbonylation reactor, the methyl acetate hydrolysis reaction is shifted toward acetic acid by coupling the dehydration and hydrolysis steps, minimizing the size of the recycle stream back to the carbonylation reactor, the hydrolysis/dehydration is conducted in the absence of carbon monoxide which maximizes the rate by avoiding dilution with carbon monoxide. In FIG. 10, methyl acetate recycle to the carbonylation reactor is minimized. As used herein, the term "lights" is contemplated to include, but is not limited to, carbon monoxide, hydrogen, methane, carbon dioxide, dimethyl ether and the like.

Another embodiment of this invention involves a process for converting a feedstock stream comprising at least one of an alcohol and ester and mixtures thereof to a product stream comprising at least one of an acid and acid anhydride and mixtures thereof which comprises (a) feeding at least a portion of a first feedstock stream comprising at least one of an ester, acid, acid anhydride, alcohol, ether, water and mixtures thereof and at least a portion of a second feedstock stream comprising an alcohol to a hydrolysis/dehydration reaction zone, (b) reacting in the hydrolysis/dehydration reaction zone in the presence of a catalyst comprising an ester hydrolysis catalytic component and an alcohol dehydration catalytic component said first and second feedstock streams under conditions of temperature and pressure sufficient to produce a crude product stream comprising at least one of an ester, acid, acid anhydride, alcohol, ether, water and mixtures thereof (containing more acid and more ether than said first feedstock stream), (c) withdrawing from the hydrolysis/dehydration reaction zone said crude product stream and feeding at least a portion of the withdrawn stream to an absorption separation zone wherein said withdrawn stream is contacted countercurrently or co-currently with an organic solvent, (d) withdrawing from the absorption separation zone an overhead fraction comprising at least one of an ether, ester, alcohol and water and feeding at least a portion of the withdrawn stream to an ether separation zone, (e) withdrawing from the ether separation zone an overhead fraction comprising an ether-rich stream, (f) withdrawing from the ether separation zone a bottoms fraction comprising at least one of an ester, alcohol and water and optionally recycling at least a portion of the withdrawn bottoms fraction to said hydrolysis/dehydration reaction zone, (g) withdrawing from the absorption separation zone a bottoms fraction comprising at least one of an ester, alcohol, organic solvent and water and feeding at least a portion of the withdrawn stream to an ester/alcohol separation zone, (h) withdrawing from the ester/alcohol separation zone an overhead fraction comprising at least one of an ester, alcohol and water and optionally recycling at least a portion of the withdrawn overhead fraction to said hydrolysis/dehydration reaction zone, (i) withdrawing from the ester/alcohol separation zone a bottoms fraction comprising at least one of an acid and organic solvent and feeding at least a portion of the withdrawn bottoms fraction to an acid separation zone, (j) withdrawing from the acid separation zone a bottoms fraction comprising an organic solvent and optionally recycling at least a portion of the withdrawn bottoms fraction to said absorption separation zone, and (k) withdrawing from the acid separation zone an overhead fraction comprising said product stream. An organic solvent separation zone may be incorporated into this process scheme. For example, at least a portion of the bottoms fraction from the absorption separation zone can be fed to an organic solvent separation zone. An overhead fraction comprising the organic solvent from the separation zone can be recycled to the absorption separation zone and a bottoms fraction comprising a mixture of an ester, alcohol, acid and organic solvent can be fed to the ester/alcohol separation zone. A unique embodiment of this invention involves the coupled hydrolysis/dehydration reaction zone. An illustrative process scheme of this embodiment is set forth in FIG. 11.

Figure 11:
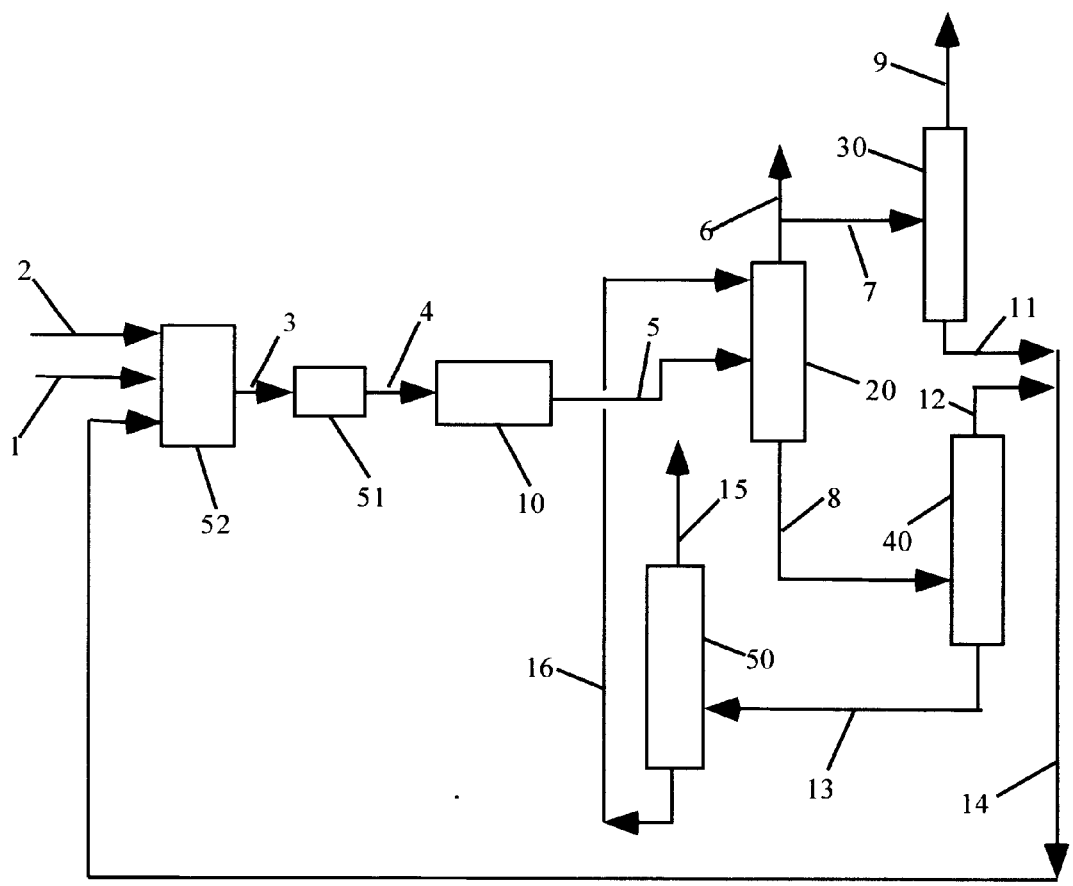
FIG. 11 is a schematic representation of a process flow diagram to make acetic acid from a methanol and methyl acetate feedstock using a coupled hydrolysis/dehydration reaction system.

In FIG. 11, which is a simplified flow diagram of an embodiment of this invention involving methyl acetate hydrolysis/methanol dehydration with dimethyl ether removal by absorption and distillation and recovery of acetic acid by distillation, a process for the preparation of acetic acid from a methyl acetate and methanol feed stream is shown. Methanol and/or methyl acetate are supplied from a carbonylation reactor (not shown) as described herein or from an external source, for example, another process unit or obtained commercially. The feedstock stream containing methanol and the feedstock stream containing acetic acid, methyl acetate, methanol, dimethyl ether and water are fed via lines 1 and 2 respectively to a hydrolysis/dehydration reactor 10. Prior to feeding into reactor 10, the feedstock streams may pass through one or more heat exchangers. Reactor 10 contains an ester hydrolysis catalyst and alcohol dehydration catalyst and is maintained at pre-selected reaction conditions of temperature and pressure, e.g., a temperature from about 50° C. to about 400° C. and a pressure from about 1 to about 10,000 psig, so that a reaction takes place in which the feedstocks are converted to a product stream containing acetic acid, dimethyl ether, methanol, methyl acetate and water. Hydrolysis of methyl acetate and dehydration of methanol can be carried out as a liquid, gas/liquid, or gas phase reaction with a homogeneous or heterogeneous acidic catalyst. The concentration of ester hydrolysis catalyst and alcohol dehydration catalyst is not narrowly critical and will depend on the desired productivity and other reaction variables. The ester hydrolysis catalyst and alcohol dehydration catalyst can be the same or different. The product stream from hydrolysis/dehydration reactor 10 is fed via line 5 to an absorption separation unit 20 to give a dimethyl ether-containing overhead fraction and an acetic acid-containing bottoms fraction. The overhead fraction is fed via line 7 to ether distillation column 30 and the bottoms fraction is fed via line 8 to ester/alcohol distillation column 40. The bottoms fraction can optionally be phase separated in a decanter (not shown) and the organic solvent can be recycled to absorption separation unit 20. The ether distillation column 30 is operated at a pressure of from 0 to about 300 psi to keep dimethyl ether liquefied so that it can be pumped via line 9 to the carbonylation reactor (not shown). Removing dimethyl ether allows for high conversion of methyl acetate to acetic acid. An overhead fraction containing dimethyl ether from ether distillation column 30 is recycled via line 9 to carbonylation reactor (not shown) and/or to a synthesis gas generation unit (not shown). A bottoms fraction containing methyl acetate, methanol and water is taken from ether distillation column 30 and sent via lines 11 and 14 to the hydrolysis/dehydration reactor 10 (via heat exchangers 51 and 52). A bottoms fraction containing methyl acetate, methanol, organic solvent, e.g., undecane, and acetic acid is taken from absorption unit 20 and sent via line 8 to the ester/alcohol distillation unit 40. An overhead fraction containing methyl acetate, methanol, organic solvent and water removed from ester/alcohol distillation column 40 is recycled via lines 12 and 14 to the hydrolysis/dehydration reactor 10. A bottoms fraction containing acetic acid and organic solvent, e.g., undecane, is taken from ester/alcohol distillation unit 40 and sent via line 13 to the acid distillation unit 50. A bottoms fraction containing organic solvent from acid distillation column 50 exits via line 16 and optionally is recycled to absorption unit 20. An overhead fraction containing acetic acid from acid distillation column 50 exits via line 15. The overhead fraction can be further refined by known methods depending on the desired acetic acid purity. An overhead purge stream may be taken from the absorption unit 20 to control the buildup of inerts.

The advantages of conducting a process as depicted by FIG. 11 include it being a simple configuration utilizing a hydrolysis/dehydration reactor to convert methyl acetate to acetic acid and methanol to dimethyl ether. In FIG. 11, methyl acetate recycle to the carbonylation reactor is minimized.

Another embodiment of this invention involves a process for converting a feedstock stream comprising at least one of an alcohol and ester and mixtures thereof to a product stream comprising at least one of an acid and acid anhydride and mixtures thereof which comprises (a) feeding at least a portion of a first feedstock stream comprising at least one of an ester, acid, acid anhydride, alcohol, ether, water and mixtures thereof to a hydrolysis reaction zone, (b) reacting in the hydrolysis reaction zone in the presence of an ester hydrolysis catalyst said first feedstock stream under conditions of temperature and pressure sufficient to produce a crude product stream comprising at least one of an ester, acid, acid anhydride, alcohol, water and mixtures thereof (containing more acid than said first feedstock stream), (c) withdrawing from the hydrolysis reaction zone said crude product stream and feeding at least a portion of the withdrawn stream to a lights separation zone, (d) withdrawing from the lights separation zone an overhead fraction comprising at least one of an ester, alcohol and water and feeding at least a portion of the withdrawn stream to a dehydration reaction zone, (e) feeding at least a portion of a second feedstock stream comprising an alcohol to said dehydration reaction zone, (f) reacting in the dehydration reaction zone in the presence of an alcohol dehydration catalyst said second feedstock stream and said overhead fraction from said lights separation zone under conditions of temperature and pressure sufficient to produce a crude product stream comprising at least one of an ether, ester, acid, acid anhydride, alcohol, water and mixtures thereof (containing more ether than said overhead fraction from said lights separation zone and said second feedstock stream), (g) withdrawing from the dehydration reaction zone said crude product stream and feeding at least a portion of the withdrawn stream to an ether separation zone, (h) withdrawing from the ether separation zone an overhead fraction comprising an ether-rich stream, (i) withdrawing from the ether separation zone a bottoms fraction comprising at least one of an ester, alcohol and water and optionally recycling at least a portion of the withdrawn bottoms fraction to said lights separation zone, (j) withdrawing from the lights separation zone a bottoms fraction comprising an acid and water and feeding at least a portion of the withdrawn stream to an acid separation zone, (k) withdrawing from the acid separation zone a fraction comprising water and optionally recycling at least a portion of the withdrawn fraction to said hydrolysis reaction zone, and (l) withdrawing from the acid separation zone a fraction comprising said product stream. The product stream can undergo further purification depending on the product quality desired. A unique embodiment of this invention involves the decoupled hydrolysis reaction zone and dehydration reaction zone. For purposes of this invention, it is understood that both dehydration and hydrolysis reactions can occur in the dehydration reaction zone. An illustrative process scheme of this embodiment is set forth in FIG. 12.

Figure 12:
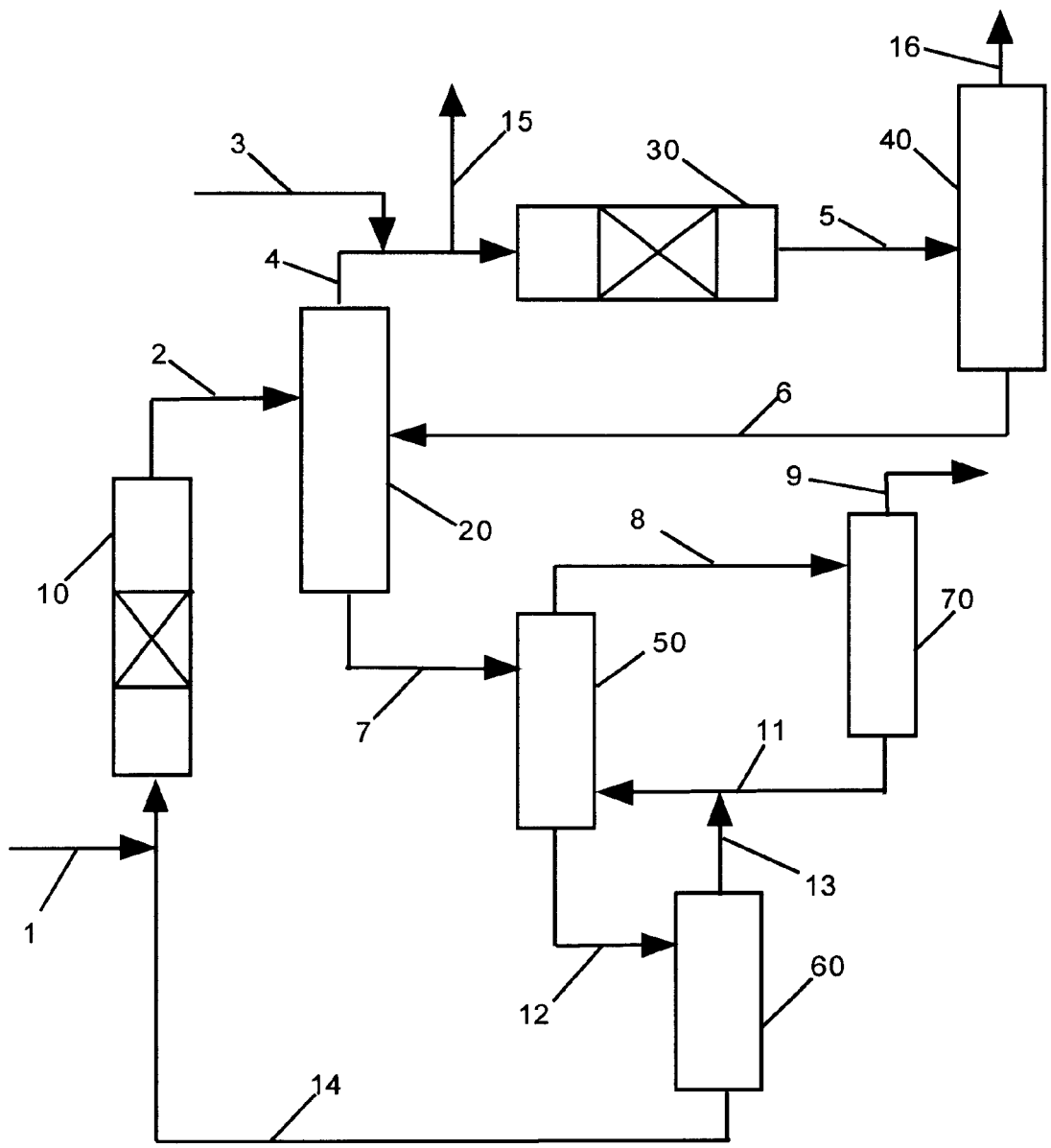
FIG. 12 is a schematic representation of a process flow diagram to make acetic acid from a methanol and methyl acetate feedstock using a decoupled hydrolysis reaction system and dehydration reaction system.

In FIG. 12, which is a simplified flow diagram of an embodiment of this invention involving decoupled methyl acetate hydrolysis and methanol dehydration with dimethyl ether removal by distillation and recovery of acetic acid by distillation, a process for the preparation of acetic acid from a methyl acetate and methanol feed stream is shown. Methanol and/or methyl acetate are supplied from a carbonylation reactor (not shown) as described herein or from an external source, for example, another process unit or obtained commercially. The feedstock stream containing acetic acid, methyl acetate, methanol, dimethyl ether and water is fed via lines 1 and 14 to a hydrolysis reactor 10. Reactor 10 contains an ester hydrolysis catalyst and is maintained at pre-selected reaction conditions of temperature and pressure, e.g., a temperature from about 50° C. to about 400° C. and a pressure from about 1 to about 10,000 psig, so that a reaction takes place in which the feedstock is converted to a product stream containing acetic acid, dimethyl ether, methanol, methyl acetate and water. Hydrolysis of methyl acetate can be carried out as a liquid, gas/liquid, or gas phase reaction with a homogeneous or heterogeneous acidic catalyst. The concentration of ester hydrolysis catalyst is not narrowly critical and will depend on the desired productivity and other reaction variables. The product stream from hydrolysis reactor 10 is fed via line 2 to lights distillation column 20 to give a methanol-containing overhead fraction and an acetic acid-containing bottoms fraction. The overhead fraction is fed via line 4 to dehydration reactor 30 and the bottoms fraction is fed via line 7 to an extraction column 50. A feedstock stream containing methanol is fed via lines 3 and 4 to dehydration reactor 30. A stream containing methanol, methyl acetate and water may optionally be taken from line 4 and sent via line 15 to a carbonylation reactor (not shown). Reactor 30 contains an alcohol dehydration catalyst and is maintained at pre-selected reaction conditions of temperature and pressure, e.g., a temperature from about 50° C. to about 400° C. and a pressure from about 1 to about 10,000 psig, so that a reaction takes place in which the feedstock is converted to an product stream containing dimethyl ether, methanol, methyl acetate, acetic acid and water. Dehydration of methanol can be carried out as a liquid, gas/liquid, or gas phase reaction with a homogeneous or heterogeneous acidic catalyst. The concentration of alcohol dehydration catalyst is not narrowly critical and will depend on the desired productivity and other reaction variables. The ester hydrolysis catalyst described above and alcohol dehydration catalyst can be the same or different. The product stream from dehydration reactor 30 is fed via line 5 to ether distillation column 40 to give an ether-rich overhead fraction and an acetic acid-containing bottoms fraction. The ether distillation column 40 is operated at a pressure of from 0 to about 300 psi to keep dimethyl ether liquefied so that it can be pumped via line 16 to the carbonylation reactor (not shown). An overhead fraction containing dimethyl ether from ether distillation column 40 is recycled via line 16 to carbonylation reactor (not shown) and/or to a synthesis gas generation unit (not shown). A bottoms fraction containing acetic acid, methyl acetate, methanol and water is taken from ether distillation column 40 and sent via line 6 to the lights distillation column 20. A bottoms fraction containing acetic acid and water is taken from lights distillation column 20 and sent via line 7 to extraction column 50. An organic solvent, e.g., methyl isobutyl ketone, is employed in extraction unit 50 to facilitate removal of acetic acid. An overhead fraction containing acetic acid and organic solvent is removed from extraction unit 50 and is sent via line 8 to acid distillation column 70. An overhead fraction containing acetic acid product from acid distillation column 70 exits via line 9. The overhead fraction can be further refined by known methods depending on the desired acetic acid purity. A bottoms fraction containing organic solvent from acid distillation column 70 exits via line 11 and optionally is recycled to extraction unit 50. A bottoms fraction containing water and organic solvent from extraction unit 50 exits via line 12 and is sent to solvent distillation column 60. An overhead fraction containing organic solvent is removed from distillation column 60 and is sent via lines 13 and 11 to extraction unit 50. A bottoms fraction containing water from distillation column 60 exits via line 14 and optionally is recycled to hydrolysis reactor 10.

The advantages of conducting a process as depicted by FIG. 12 include it being a simple configuration utilizing a decoupled hydrolysis reactor and dehydration reactor to convert methyl acetate to acetic acid and methanol to dimethyl ether, conducting hydrolysis in the liquid phase and dehydration in the vapor phase, and minimizing the size of the recycle stream. In FIG. 12, methyl acetate recycle to the carbonylation reactor is minimized.

Another embodiment of this invention involves a process for converting a feedstock stream comprising at least one of an alcohol and ester and mixtures thereof to a product stream comprising at least one of an acid and acid anhydride and mixtures thereof which comprises (a) feeding at least a portion of a feedstock stream comprising at least one of an ester, acid, acid anhydride, alcohol, ether, water and mixtures thereof to an extractive separation zone, (b) withdrawing from the extractive separation zone a bottoms fraction comprising at least one of an alcohol, acid and water and feeding at least a portion of the withdrawn stream to an alcohol separation zone, (c) withdrawing from the alcohol separation zone an overhead fraction comprising an alcohol-rich stream, (d) withdrawing from the alcohol separation zone a bottoms fraction comprising water and optionally recycling at least a portion of the withdrawn bottoms fraction to said extractive separation zone, (e) withdrawing from the extractive separation zone an overhead fraction comprising at least one of an ester, alcohol and water and feeding at least a portion of the withdrawn stream to a hydrolysis reaction zone, (f) reacting in the hydrolysis reaction zone in the presence of an ester hydrolysis catalyst said overhead fraction from said extractive separation zone under conditions of temperature and pressure sufficient to produce a crude product stream comprising at least one of an ester, acid, acid anhydride, alcohol, water and mixtures thereof (containing more acid than said feedstock stream), (g) withdrawing from the hydrolysis reaction zone said crude product stream and feeding at least a portion of the withdrawn stream to a lights separation zone, (h) withdrawing from the lights separation zone an overhead fraction comprising at least one of an ester, alcohol and water and optionally recycling at least a portion of the withdrawn stream to said extractive separation zone, (i) withdrawing from the lights separation zone a bottoms fraction comprising an acid and water and feeding at least a portion of the withdrawn stream to an acid separation zone, (j) withdrawing from the acid separation zone a fraction comprising water and optionally recycling at least a portion of the withdrawn fraction to said hydrolysis reaction zone, and (k) withdrawing from the acid separation zone a fraction comprising said product stream. The product stream can undergo further purification depending on the product quality desired. A unique embodiment of this invention involves the hydrolysis reaction zone. An illustrative process scheme of this embodiment is set forth in FIG. 13.

Figure 13:
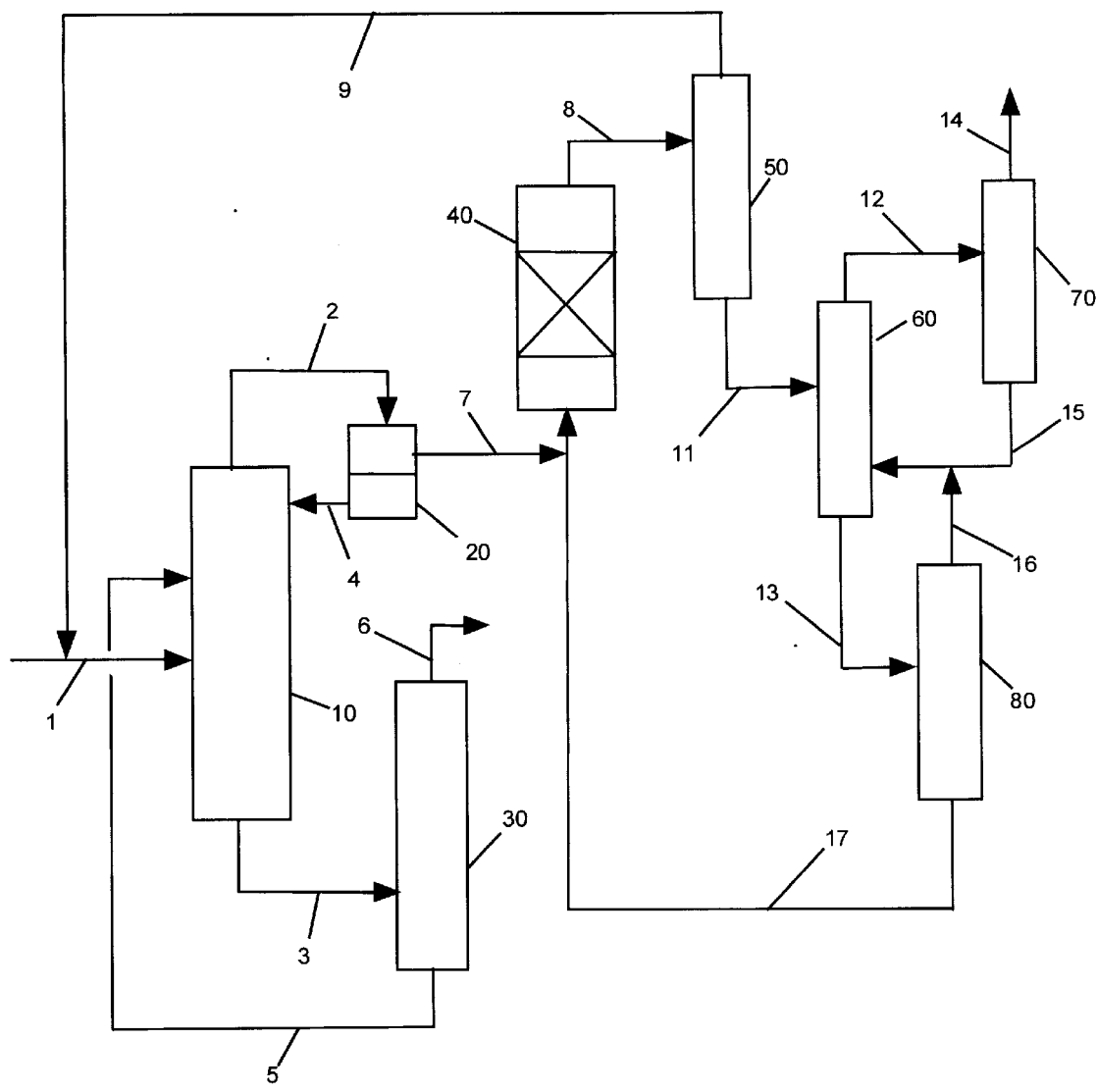
FIG. 13 is a schematic representation of a process flow diagram to make acetic acid from a methyl acetate-containing feedstock using a hydrolysis reaction system.

In FIG. 13, which is a simplified flow diagram of an embodiment of this invention involving methyl acetate hydrolysis and recovery of acetic acid by distillation, a process for the preparation of acetic acid from a methyl acetate feed stream is shown. Methanol and methyl acetate are supplied from a carbonylation reactor (not shown) as described herein or from an external source, for example, another process unit or obtained commercially. The feedstock stream containing acetic acid, methyl acetate, methanol, dimethyl ether and water is fed via line 1 to extractive distillation column 10. Water is employed in extractive distillation column 10 to facilitate removal of methanol. A bottoms fraction containing methanol and water is taken from extractive distillation column 10 and sent via line 3 to the methanol distillation column 30. A methanol-rich stream is taken overhead from methanol distillation column 30 and optionally recycled via line 6 to a carbonylation reaction zone (not shown). A bottoms fraction containing water is taken from methanol distillation column 30 and sent via line 5 to extractive distillation column 10. An overhead fraction containing methyl acetate, methanol and water is taken from extractive distillation column 10 and sent via line 2 to a decanter 20. From phase separation in decanter 20, a bottom layer containing water is removed and sent via line 4 to extractive distillation column 10 and a top layer containing methyl acetate and methanol (and some water) is removed and sent via line 7 to a hydrolysis reactor 40. Reactor 40 contains an ester hydrolysis catalyst and is maintained at pre-selected reaction conditions of temperature and pressure, e.g., a temperature from about 50° C. to about 400° C. and a pressure from about 1 to about 10,000 psig, so that a reaction takes place in which the feedstock is converted to a product stream containing acetic acid, dimethyl ether, methanol, methyl acetate and water. Hydrolysis of methyl acetate can be carried out as a liquid, gas/liquid, or gas phase reaction with a homogeneous or heterogeneous acidic catalyst. The concentration of ester hydrolysis catalyst is not narrowly critical and will depend on the desired productivity and other reaction variables. The product stream from hydrolysis reactor 40 is fed via line 8 to lights distillation column 50 to give a methanol-containing overhead fraction and an acetic acid-containing bottoms fraction. The overhead fraction is fed via lines 9 and 1 to extractive distillation column 10 and the bottoms fraction is fed via line 11 to an extraction column 60. A bottoms fraction containing acetic acid and water is taken from lights distillation column 50 and sent via line 11 to extraction column 60. An organic solvent, e.g., methyl isobutyl ketone, is employed in extraction unit 60 to facilitate removal of acetic acid. An overhead fraction containing acetic acid and organic solvent is removed from extraction unit 60 and is sent via line 12 to acid distillation column 70. An overhead fraction containing acetic acid product from acid distillation column 70 exits via line 14. The overhead fraction can be further refined by known methods depending on the desired acetic acid purity. A bottoms fraction containing organic solvent from acid distillation column 70 exits via line 15 and optionally is recycled to extraction unit 60. A bottoms fraction containing water and organic solvent from extraction unit 60 exits via line 13 and is sent to solvent distillation column 80. An overhead fraction containing organic solvent is removed from distillation column 80 and is sent via lines 16 and 15 to extraction unit 60. A bottoms fraction containing water from distillation column 80 exits via line 17 and optionally is recycled to hydrolysis reactor 40.

The advantages of conducting a process as depicted by FIG. 13 include it being a simple configuration utilizing a hydrolysis reactor to convert methyl acetate to acetic acid, conducting hydrolysis in the liquid phase, and minimizing the size of the recycle stream. In FIG. 13, methyl acetate recycle to the carbonylation reactor is minimized.

Another embodiment of this invention involves a process for converting a feedstock stream comprising at least one of an alcohol and ester and mixtures thereof to a product stream comprising at least one of an acid and acid anhydride and mixtures thereof which comprises (a) feeding at least a portion of a first feedstock stream comprising at least one of an ester, acid, acid anhydride, alcohol, ether, water and mixtures thereof and at least a portion of a second feedstock stream comprising an alcohol to a hydrolysis/dehydration reaction zone, (b) reacting in the hydrolysis/dehydration reaction zone in the presence of a catalyst comprising an ester hydrolysis catalytic component and an alcohol dehydration catalytic component said first and second feedstock streams under conditions of temperature and pressure sufficient to produce a crude product stream comprising at least one of an ester, acid, acid anhydride, alcohol, ether, water and mixtures thereof (containing more acid and more ether than said first feedstock stream), (c) withdrawing from the hydrolysis/dehydration reaction zone an overhead fraction comprising an ether-rich stream, (d) withdrawing from the hydrolysis/dehydration reaction zone a bottoms fraction comprising at least one of an acid, ester, alcohol and water and feeding at least a portion of the withdrawn stream to an acid separation zone, (e) withdrawing from the acid separation zone an overhead fraction comprising at least one of an ester, alcohol and water and optionally recycling at least a portion of the withdrawn overhead fraction to said hydrolysis/dehydration reaction zone, and (f) withdrawing from the acid separation zone a bottoms fraction comprising said product stream. A unique embodiment of this invention involves the coupled hydrolysis/dehydration reaction zone with simultaneous removal of an ether-rich stream from the reaction zone. An illustrative process scheme of this embodiment is set forth in FIG. 14.

Figure 14:
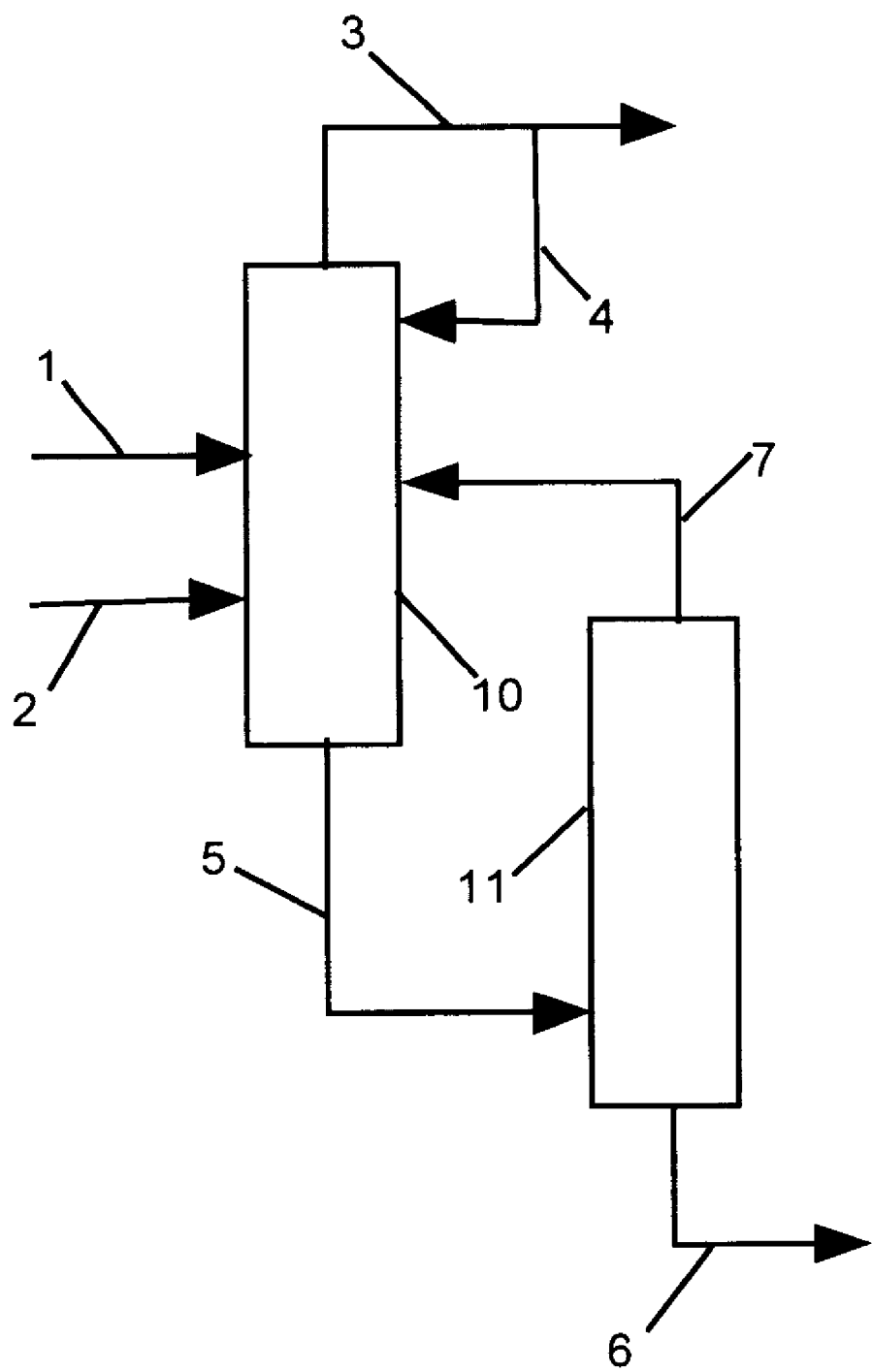
FIG. 14 is a schematic representation of a process flow diagram to make acetic acid from a methanol and methyl acetate feedstock using a coupled hydrolysis/dehydration reaction system.

In FIG. 14, which is a simplified flow diagram of an embodiment of this invention involving methyl acetate hydrolysis/methanol dehydration with dimethyl ether removal by distillation and recovery of acetic acid by distillation, a process for the preparation of acetic acid from a methyl acetate and methanol feed stream is shown. Methanol and/or methyl acetate are supplied from a carbonylation reactor (not shown) as described herein or from an external source, for example, another process unit or obtained commercially. The feedstock stream containing methanol and the feedstock stream containing acetic acid, methyl acetate, methanol, dimethyl ether and water are fed via lines 1 and 2 respectively to a hydrolysis/dehydration reactor 10. A rectification zone (not shown) can be included in reactor 10. Reactor 10 contains an ester hydrolysis catalyst and alcohol dehydration catalyst and is maintained at pre-selected reaction conditions of temperature and pressure, e.g., a temperature from about 50° C. to about 400° C. and a pressure from about 1 to about 10,000 psig, so that a reaction takes place in which the feedstocks are converted to a product stream containing acetic acid, methanol, methyl acetate and water. Hydrolysis of methyl acetate and dehydration of methanol can be carried out as a liquid, gas/liquid, or gas phase reaction with a homogeneous or heterogeneous acidic catalyst. The concentration of ester hydrolysis catalyst and alcohol dehydration catalyst is not narrowly critical and will depend on the desired productivity and other reaction variables. The ester hydrolysis catalyst and alcohol dehydration catalyst can be the same or different. An overhead fraction containing dimethyl ether is removed via line 3 from hydrolysis/dehydration reactor 10 and optionally sent to a carbonylation reactor (not shown) and/or to a synthesis gas generation unit (not shown). Removing dimethyl ether allows for high conversion of methyl acetate to acetic acid. A portion of the withdrawn overhead stream removed via line 3 from hydrolysis/dehydration reactor 10 may optionally be recycled via line 4 to reactor 10. A bottoms fraction containing acetic acid, methyl acetate, methanol and water is taken from hydrolysis/dehydration reactor 10 and sent via line 5 to the distillation unit 11. An overhead fraction containing methyl acetate, methanol and water removed from distillation column 11 is recycled via line 7 to the hydrolysis/dehydration reactor 10. A bottoms fraction containing acetic acid is taken via line 6 from distillation unit 11. The bottoms fraction can be further refined by known methods depending on the desired acetic acid purity.

The advantages of conducting a process as depicted by FIG. 14 include it being a simple configuration utilizing a hydrolysis/dehydration reactor to convert methyl acetate to acetic acid and methanol to dimethyl ether and conducting the hydrolysis/dehydration reaction in the liquid phase to enable stripping of dimethyl ether. In FIG. 14, methyl acetate recycle to the carbonylation reactor is minimized.

The particular reaction conditions for the various embodiments described herein are not narrowly critical and can be any effective reaction conditions sufficient to produce at least one of an ester, acid, acid anhydride and mixtures thereof. The exact reaction conditions will be governed by the best compromise between achieving high catalyst selectivity, activity, lifetime and ease of operability, as well as the intrinsic reactivity of the starting materials in question and the stability of the starting materials and the desired reaction product to the reaction conditions.

Synthesis Gas Generation

Processes for reforming hydrocarbons to produce synthesis gas are well known. Each has its advantages and disadvantages and the choice of using a particular reforming process is dictated by economic and available feed stream considerations, as well as by the desired mole ratio of $H_2$:CO in the feedstock resulting from the reforming reaction. Steam reforming typically produces a hydrogen to carbon monoxide mole ratio greater than about 2.5:1. Partial oxidation reforming can typically produce smaller hydrogen to carbon monoxide mole ratios. Partial oxidation reforming of alkane is a controlled combustion reaction in which a feed stream of alkane hydrocarbon, such as methane, and oxygen is introduced into a combustion chamber. The combustion conditions are controlled to selectively make the desired hydrogen-carbon monoxide ratio in the feedstock. Steam reforming and partial oxidation of hydrocarbons are well known processes and are described, for example, in Kirk-Othmer, Encyclopedia of Chemical Technology, Fourth Edition, 1996, the pertinent portions of which are incorporated herein by reference.

Any hydrocarbon-containing feed stream that can be converted into a feedstock comprising carbon monoxide and hydrogen, most preferably a synthesis gas (or "syn gas"), is useful in the processes of the invention. The ratio of hydrogen to carbon monoxide in the reaction zone is in the range of about 50:1 to 1:50, preferably in the range of about 20:1 to 1:20, more preferably in the range of about 10:1 to 1:10. Useful feed streams include natural gas (mainly methane, but natural gas composition can vary depending on location and source), naphtha, refinery off-gas, LPG, gas oil, vacuum residuals, shale oils, asphalts, various types of fuel oils, and hydrocarbon containing process recycle streams. In an embodiment, methanol can be converted into feed components comprising carbon monoxide and hydrogen, e.g., synthesis gas. Further, hydrogen may be formed in situ, for example, by water-gas shift.

Feedstocks comprising carbon monoxide and hydrogen, e.g., synthesis gas, may undergo purification prior to being fed to any reaction zones. For use in the processes of this invention, the synthesis gas should be essentially free of catalyst poisons and inhibitors such as hydrogen sulfide, carbonyl sulfide, metal carbonyls, e.g., iron carbonyl and nickel carbonyl, ammonia, basic organic compounds, e.g., methyl amine and ethyl amine, and generally any compounds that will neutralize an acid. Synthesis gas purification may be carried out by processes known in the art. See, for example, Weissermel, K. and Arpe H.-J., Industrial Organic Chemistry, Second, Revised and Extended Edition, 1993, pp. 19–21.

Alcohol/Ether Carbonylation

The carbonylation reaction can be carried out by passing the substrate to be carbonylated, e.g., alcohol and/or ether, and carbon monoxide and optionally hydrogen over the catalyst as a vapor phase reaction or as a liquid phase reaction, e.g., slurry reaction. The substrate comprising an alcohol, ether, or mixtures thereof can be formed in situ by feeding synthesis gas to an appropriate catalyst that is coupled to the carbonylation catalyst either in the same or different reactors. If desired, such substrates, e.g., methanol, and/or synthesis gas can be obtained from a different source and fed directly to the carbonylation catalyst.

With reference to FIG. 1, the temperature in the single reaction zone is selected from the range of from about 100° C. to about 500° C., preferably a temperature in the range of from about 150° C. to about 400° C., with an especially preferred temperature in the range of from about 175° C. to about 375° C. The gas hourly space velocity (GHSV) of the feedstock passing through the reaction zone can vary significantly, depending upon a variety of factors such as, for example, reaction conditions, composition of the feedstock and quantity and type of catalyst being used. The GHSV can be maintained at any rate in the range of from about 1 to about 30,000 $hr^{-1}$ or more, preferably will be maintained at a rate of at least about 500 $hr^{-1}$, and more preferably will be maintained at a rate of at least 1,000 $hr^{-1}$.

The pressure in the single reaction zone may be selected from the range of from about 1 to about 10,000 psig, preferably a pressure in the range of from about 50 to about 5,000 psig, with an especially preferred pressure in the range of from about 500 to about 3,000 psig. The hydrogen and carbon monoxide partial pressures should be sufficient to enable the production of one or more oxygenates. Additionally, the hydrogen partial pressure should be sufficient to impart stabilization to the carbonylation catalytic component. Illustrative hydrogen partial pressures may range, for example, from about 0.1 psig or less to about 9000 psig or greater, or from about 0.1 psig or less to about 4500 psig or greater, or from about 0.1 psig or less to about 2700 psig or greater. Illustrative carbon monoxide partial pressures may range, for example, from about 0.1 psig or less to about 9000 psig or greater, or from about 0.1 psig or less to about 4500 psig or greater, or from about 0.1 psig or less to about 2700 psig or greater. Hydrogen and carbon monoxide may be fed separately to the single reactor or in combination, e.g., synthesis gas.

With reference to FIGS. 2–9, the temperature in the carbonylation reaction zone is selected from the range of from about 100° C. to about 500° C., preferably a temperature in the range of from about 150° C. to about 400° C., with an especially preferred temperature in the range of from about 175° C. to about 375° C. The gas hourly space velocity (GHSV) of the feedstock (liters of feedstock/hr/liter of catalyst) passing through the carbonylation reaction zone can vary significantly, depending upon a variety of factors such as, for example, reaction conditions, composition of the feedstock and quantity and type of catalyst being used. The GHSV can be maintained at any rate in the range of from about 1 to about 30,000 $hr^{-1}$ or more, preferably will be maintained at a rate of at least about 500 $hr^{-1}$, and more preferably will be maintained at a rate of at least 1,000 $hr^{-1}$. Likewise, the liquid hourly space velocity (LHSV) of the feedstock passing through the carbonylation reaction zone can vary significantly, depending upon a variety of factors such as, for example, reaction conditions, composition of the feedstock and quantity and type of catalyst being used. The LHSV to the reactor when the feed is vaporized prior to entering or within the reactor may range from about 0.01 to about 100 $hr^{-1}$, preferably from about 0.01 to about 10 $hr^{-1}$. The GHSV and LHSV accommodate the amount of alcohol, ether and mixtures thereof fed to the carbonylation reactor.

The pressure in the carbonylation reaction zone may be selected from the range of from about 1 to about 10,000 psig, with an especially preferred pressure in the range of from about 50 to about 5,000 psig, with an especially preferred pressure in the range of from about 500 to about 3,000 psig. The carbon monoxide partial pressure should be sufficient to permit the reaction with an alcohol, ether, or mixtures thereof to produce one or more oxygenates. It has been unexpectedly found that when the carbonylation reaction is carried out in the presence of hydrogen, stabilization is impaired to the carbonylation catalyst. Accordingly, the hydrogen partial pressure should be sufficient to impart stabilization to the carbonylation catalyst. Illustrative hydrogen partial pressures may range, for example, from about 0.1 psig or less to about 9000 psig or greater, or from about 0.1 psig or less to about 4500 psig or greater, or from about 0.1 psig or less to about 2700 psig or greater. Illustrative carbon monoxide partial pressures may range, for example, from about 0.1 psig or less to about 9000 psig or greater, or from about 0.1 psig or less to about 4500 psig or greater, or from about 0.1 psig or less to about 2700 psig or greater. Hydrogen and/or carbon monoxide may be fed separately to the carbonylation reactor or in combination, e.g., as synthesis gas or as part of a feed stream from a separate reactor as described herein.

For purposes of this invention, GHSV is gas hourly space velocity which is the rate of gas flow over the catalyst. It is determined by dividing the volume of gas (at 25° C. and 1 atmosphere) which passes over the catalyst in one hour by the volume of the catalyst. LHSV is liquid hourly space velocity which is the rate that the liquid organic substrate is fed to the carbonylation reactor. It is determined by dividing the liquid volume pumped in one hour by the volume of catalyst.

The carbonylation catalysts and carbonylation catalytic components useful in the processes of this invention include solid acidic materials, for example, solid super acids, heteropoly acids, clays, zeolites, molecular sieves, and the like. See, for example, U.S. patent application Ser. No. 09/220,438, filed Dec. 24, 1998, the disclosure of which is incorporated herein be reference. Two or more permissible carbonylation catalysts or carbonylation catalytic components may be used in a combined form. Illustrative of suitable carbonylation catalysts and carbonylation catalytic components include those permissible solid acidic materials described in Tsutomu Yamaguchi, "Recent Progress in Solid Superacid", Applied Catalysis, 61, (1990), 1 and "Zeolite, Clay, and Heteropoly Acid in Organic Reactions", by Yusuke Izumi, Kazuo Urabe and Makato Onaka, VCH Publishers Inc., 1992, the pertinent portions of which are incorporated herein by reference.

The carbonylation catalysts and carbonylation catalytic components exhibit an acid strength of less than or equal to −5.0 (Ho≦−5.0), preferably less than or equal to −10.0 (Ho≦−10.0), and more preferably less than or equal to −12.5 (Ho≦−12.5). Acid strength of solid acids can be evaluated by conventional methods such as by establishing Hammett acidity functions (Ho) using organic indicators as described below.

When the color of a catalyst sample subjected to the determination is white, this sample is immersed in benzene and a benzene solution containing an acid-base indicator of a known pKa value is added thereto. The sample is kept under observation until the indicator on the surface of the sample assumes the color of acidity. The smallest value of pKa at which the color of acidity is assumed is reported as the acid strength of the sample. The indicators (pKa) which are usable for this determination include, for example, m-nitrotoluene (−12.0), p-nitrotoluene (−12.4), p-nitrochlorobenzene (−12.7), m-nitrochlorobenzene (−13.2), 2,4-dinitrotoluene (−13.8), and 1,3,5-trinitrobenzene (−16.0).

Solid super acid catalysts are preferred carbonylation catalysts and carbonylation catalytic components for use in this invention. The preferred solid super acids are generally considered to have an acidity stronger than 100% $H_2SO_4$, i.e., Ho<−12.5.

Illustrative examples of solid super acids are $Fe_2O_3$—$SO_4$, $SnO_2$—$SO_4$, $TiO_2$—$SO_4$, $ZrO_2$—$SO_4$ and $ZrO_2$—$B_2O_3$, $ZrO_2$—$MO_3$, $ZrO_2$—$WO_3$, $Fe_2O_3$—$WO_3$, sulfated metal oxides promoted with Pt, Fe, Mn, and halogen promoted $SiO_2$/alumina. A solid super acid impregnated with a Group 7, 8, 9, 10 and/or 11 transition metal is a particularly preferred catalyst or catalytic component. Illustrative of suitable solid super acids include those permissible solid super acids described in Tsutomu Yamaguchi, "Recent Progress in Solid Superacid", Applied Catalysis, 61, (1990), 1, supra.

The solid super acids and methods for their preparation are known. See, for example, EP Patent Application 0 685 259 A2 and U.S. Pat. No. 5,780,383, the disclosures of which are incorporated herein by reference. Preferred carbonylation catalysts and catalytic components are obtained when certain solid super acids such as Group 4, 5 and/or 6 metal oxides and mixtures thereof are impregnated with a Group 7, 8, 9, 10 and/or 11 metal and mixtures thereof. The weight percent of Group 7, 8, 9, 10 and/or 11 metals impregnated onto Group 4, 5 and/or 6 metal oxides can range from about zero to about 10 weight percent or greater, preferably from about 0.001 weight percent to about 5 weight percent. The weight percent of Group 6 metal oxides, i.e., $MoO_3$ and $WO_3$, in said Group 4, 5 and/or 6 metal oxide super acids can range from about 1 to about 40 weight percent or greater, preferably from about 4 weight percent to about 30 weight percent. The catalysts carbonylate methanol, dimethyl ether, and methyl acetate with synthesis gas in the vapor phase or in the liquid phase, e.g., as a slurry. The preferred solid super acids are based on Group 4 metal oxides impregnated with Mo or W. Thus, the preferred solid super acids are Ti—W, Ti—Mo, Zr—W, Zr—Mo, Hf—W, and Hf—Mo oxides or mixtures thereof.

As indicated above, no halide promoters, e.g., methyl iodide, are required in the liquid or vapor phases of the feedstock streams and/or recycle streams of the processes of this invention, thus providing substantial economic benefits in the design of equipment to carry out the processes. It is understood that halides which are fixed onto the catalyst or otherwise are an integral part of the catalyst are permissible in the processes of this invention.

Another category of carbonylation catalysts and catalytic components include heteropoly acids such as disclosed in U.S. Pat. Nos. 5,218,140 and 5,330,955, supra. Preferred heteropoly acids exhibit an acid strength of less than or equal to −1.0 (Ho≦1.0), preferably less than or equal to −5.0 (Ho≦−5.0). Such alcohol carbonylation catalysts and catalytic components contain a polyoxometalate ion in which a metal, or mixture of metals, selected from Groups 4, 5, 6 and 7 metals is complexed with a cation from a member of Group 7, 8, 9, 10 and/or 11 metals. More preferably this alcohol carbonylation catalyst and catalytic component consists of a Group 7, 8, 9, 10 and/or 11 metal cation complexed with a heteropoly acid anion. Mixtures of heteropoly acids may be employed in the processes of this invention.

Other useful carbonylation catalysts include clays. Clays may also serve as a support for the alcohol carbonylation catalysts. Preferred clays exhibit an acid strength of less than or equal to −1.0 (Ho≦−1.0), preferably less than or equal to −5.0 (Ho≦−5.0). The weight percent of Group 7, 8, 9, 10 and/or 11 metals that may be impregnated onto clays can range from about zero to about 10 weight percent, preferably from about 0.001 weight percent to about 5 weight percent. Clay is a label applied to a generic class of materials comprised of layers of aluminosilicate with complex intercalation chemistry. In general, the layers have an overall negative charge which is balanced by hydrated cations occupying the interlayer space. The acidity of clays can be modified by exchanging the interlayer cations. Ion exchange with suitable large inorganic cations leads to pillared clays, which can be potential shape selective catalysts. Preferred pillared clays have increased surface areas and thermal stability. Careful selection of cations for clay ion exchange can lead to pillared clays with large well defined spaces between layers (referred to as galleries), that can be useful as selective catalysts. Suitable clays useful in this invention include, for example, montmorillonite, bentonite, kaolinite, and the like, including mixtures thereof. Illustrative of suitable clays include those permissible clays described in "Zeolite, Clay, and Heteropoly Acid in Organic Reactions", by Yusuke Izumi, Kazuo Urabe and Makato Onaka, VCH Publishers Inc., 1992, supra.

Still other useful carbonylation catalysts include molecular sieves of the zeolitic variety, i.e., zeolites, and molecular sieves of the non-zeolitic variety, i.e., molecular sieves. Preferred zeolites and molecular sieves exhibit an acid strength of less than or equal to −1.0 (Ho≦−1.0), preferably less than or equal to −5.0 (Ho≦−5.0). The weight percent of Group 7, 8, 9, 10 and/or 11 metals that may be impregnated onto zeolites and molecular sieves can range from about zero to about 10 weight percent, preferably from about 0.001 weight percent to about 5 weight percent. Illustrative zeolites useful in this invention include, for example, LZ-10, LZ-20, 4A, 5A, 13X, 10X, Y, SK40, SK41, chabazite, faujasite, levynite, gismondine, erionite, sodalite, analcime, gmelinite, harmotome, mordenite, epistilbite, heulandite, stilbite, edingtonite, mesolite, natrolite, scolecite, thomsonite, brewsterite, laumontite, phillipsite, the ZSM's (ZSM-5, ZSM-20, ZSM-12, and ZSM-34), and the like, including mixtures thereof. Illustrative zeolites useful in this invention are disclosed in U.S. Pat. Nos. 3,702,886, 3,972, 983, 3,832,449, 4,086,186 and 3,308,069, the disclosures of which are incorporated herein be reference.

Illustrative molecular sieves useful in this invention include, for example, the silica molecular sieves, such as silicalite (S115) as depicted in U.S. Pat. Nos. 4,061,724 and 4,073,865, the disclosures of which are incorporated herein by reference. Other molecular sieves useful in this invention include crystalline microporous molecular sieve oxides that are based on the presence of aluminophosphate in the framework of the crystal structures, e.g., those commonly known by the acronyms SAPO, MeAPO, FAPO, MAPO, MNAPO, CoAPO, ZAPO, MeAPSO, FAPSO, MAPSO, MnAPSO, CoAPSO, ZAPSO, ElAPO, ElAPSO and the like, including mixtures thereof. Such molecular sieves are described, for example, in U.S. Pat. Nos. 4,567,029, 4,440, 871, 4,500,651, 4,554,143 and 4,310,440, the disclosures of which are incorporated herein by reference.

This invention is not intended to be limited by permissible catalyst mixtures. As used herein, a catalyst comprising a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, or mixtures thereof, is intended to include, for example, (i) a mixture of two or more solid super acids impregnated with a Group 7, 8, 9, 10 and/or 11 metal, two or more heteropoly acids impregnated with a Group 7, 8, 9, 10 and/or 11 metal, two or more clays impregnated with a Group 7, 8, 9, 10 and/or 11 metal, two or more zeolites impregnated with a Group 7, 8, 9, 10 and/or 11 metal or two or more molecular sieves impregnated with a Group 7, 8, 9, 10 and/or 11 metal, (ii) a mixture of at least two of a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, (iii) a mixture of two or more solid super acids, two or more heteropoly acids, two or more clays, two or more zeolites or two or more molecular sieves, said mixture impregnated with a Group 7, 8, 9, 10 and/or 11 metal, or (iv) a mixture of at least two of a solid super acid, heteropoly acid, clay, zeolite and molecular sieve, said mixture impregnated with a Group 7, 8, 9, 10 and/or 11 metal.

Alcohol and/or Ether Synthesis

The alcohol synthesis reaction can be carried out by conventional methods by passing carbon monoxide and hydrogen over a catalyst as a vapor phase reaction or as a liquid phase reaction, e.g., slurry reaction. The alcohol synthesis reaction may be carried out either alone or in conjunction with the alcohol dehydration reaction, e.g., FIG. 1. The ether synthesis reaction can be carried out by conventional methods by passing an alcohol over a catalyst, e.g., alcohol dehydration, as a vapor phase reaction or as a liquid phase reaction, e.g., slurry reaction. The alcohol dehydration reaction may be conducted either alone or in conjunction with the alcohol synthesis reaction or ester hydrolysis reaction described below.

With reference to FIG. 1, the alcohol synthesis reaction is coupled with the alcohol dehydration reaction in one reactor compartment and this combination is further coupled with the carbonylation reaction in another reactor compartment. The temperature in the single reaction zone is selected from the range of from about 100° C. to about 500° C., preferably a temperature in the range of from about 150° C. to about 400° C., with an especially preferred temperature in the range of from about 175° C. to about 375° C. The gas hourly space velocity (GHSV) of the feedstock synthesis gas passing through the reaction zone can vary significantly, depending upon a variety of factors such as, for example, reaction conditions, composition of the feedstock and quantity and type of catalyst being used. The GHSV can be maintained at any rate in the range of from about 1 to about 30,000 hr$^{-1}$ or more, preferably will be maintained at a rate of at least about 500 hr$^{-1}$, and more preferably will be maintained at a rate of at least 1,000 hr$^{-1}$.

The pressure in the single reaction zone may be selected from the range of from about 1 to about 10,000 psig, preferably a pressure in the range of from about 50 to about 5,000 psig, with an especially preferred pressure in the range of from about 500 to about 3,000 psig. The hydrogen and carbon monoxide partial pressures should be sufficient to enable the production of one or more oxygenates. Illustrative hydrogen partial pressures may range, for example, from about 0.1 psig or less to about 9000 psig or greater, or from about 0.1 psig or less to about 4500 psig or greater, or from about 0.1 psig or less to about 2700 psig or greater. Illustrative carbon monoxide partial pressures may range, for example, from about 0.1 psig or less to about 9000 psig or greater, or from about 0.1 psig or less to about 4500 psig or greater, or from about 0.1 psig or less to about 2700 psig or greater. Hydrogen and carbon monoxide may be fed separately to the single reactor or in combination, e.g., synthesis gas.

With reference to FIGS. 2 and 3, the temperature in the alcohol synthesis reaction zone and/or the alcohol dehydration reaction zone is selected from the range of from about 100° C. to about 500° C., preferably a temperature in the range of from about 150° C. to about 400° C., with an especially preferred temperature in the range of from about 175° C. to about 375° C. The gas hourly space velocity (GHSV) of the feedstock (liters of feedstocklhr/liter of catalyst) passing through the reaction zone can vary significantly, depending upon a variety of factors such as, for example, reaction conditions, composition of the feedstock and quantity and type of catalyst being used. The GHSV can be maintained at any rate in the range of from about 1 to about 30,000 $hr^{-1}$ or more, preferably will be maintained at a rate of at least about 500 $hr^{-1}$, and more preferably will be maintained at a rate of at least 1,000 $hr^{-1}$. The pressure in the alcohol synthesis reaction zone and/or the alcohol dehydration reaction zone may be selected from the range of from about 1 to about 10,000 psig, preferably a pressure in the range of from about 50 to about 5,000 psig, with an especially preferred pressure in the range of from about 500 to about 3,000 psig.

The alcohol synthesis catalyst or alcohol synthesis catalytic component are conventional materials and can be selected from either of two groups: a first group which includes: (a) alkali and/or metal promoted $MoS_2$-based materials, (b) Group 7, 8, 9, 10 and/or 11 metals, supported or unsupported, with or without metal and alkali promoters, (c) mixed metal oxides of Co or Ni with Cu with or without a trivalent metal ion and/or alkali promoters, and (d) mixtures thereof; and a second group which includes (a) an alkali and/or metal promoted ZnCrO, MnCrO and ZnMnCrO, (b) alkali and/or metal promoted Cu/ZnO materials, and (c) mixtures thereof, and mixtures of the first and second groups. Preferably, the alcohol synthesis catalyst or alcohol synthesis catalytic component is selected from among those catalysts used commercially to make methanol from a synthesis gas, which are highly developed and their activity and selectivity are known. They include: (a) Cu/ZnO (with or without Al), (b) Cu-rare earth metals, and (c) supported Group 7, 8, 9 and/or 10 metals. In a coupled arrangement, the catalyst can be configured as a single bed or layered or intimate mixture. Illustrative alcohol synthesis catalysts or alcohol synthesis catalytic components are described, for example, in Kirk-Othmer, Encyclopedia of Chemical Technology, Fourth Edition, 1996, the pertinent portions of which are incorporated herein by reference.

The alcohol dehydration catalyst or alcohol dehydration catalytic component are conventional materials and can be selected from selected from a solid acid such as an acidic gamma alumina, fluorinated alumina, sulfate or tungstate promoted zirconia; heteropoly acids, acidic zeolites such as NaY, HY, and ZSM-5, titania or silica promoted alumina, aluminum phosphate, or tungsten oxide supported on silica-alumina, and the like. In a coupled arrangement, the catalyst can be configured as a single bed or layered or intimate mixture. Illustrative alcohol dehydration catalysts or alcohol dehydration catalytic components are described, for example, in Kirk-Othmer, Encyclopedia of Chemical Technology, Fourth Edition, 1996, the pertinent portions of which are incorporated herein by reference.

Ester Hydrolysis

The ester hydrolysis reaction can be carried out by conventional methods by passing an ester over a catalyst as a vapor phase reaction or as a liquid phase reaction, e.g., slurry reaction. The ester hydrolysis reaction may be conducted either alone or in conjunction with the alcohol dehydration reaction. In a preferred embodiment, methyl acetate can be converted into acetic acid. A unique embodiment of this invention involves a coupled ester hydrolysis and alcohol dehydration configuration in which the catalysts can be the same or different.

With reference to FIG. 5, the temperature in the ester hydrolysis reaction zone is selected from the range of from about 50° C. to about 400° C., preferably a temperature in the range of from about 70° C. to about 250° C. The feed rate sent to the ester hydrolysis reactor can vary significantly, depending upon a variety of factors such as, for example, reaction conditions, composition of the feedstock and quantity and type of catalyst being used. The liquid hourly space velocity (LHSV) to the ester hydrolysis reactor when the feed is vaporized prior to entering or within the reactor may range from about 0.001 to about 100 $hr^{-1}$, preferably from about 0.01 to about 10 $hr^{-1}$. The pressure in the ester hydrolysis reaction zone may be selected from the range of from about 1 to about 10,000 psig, preferably a pressure in the range of from about 10 to about 5,000 psig, with an especially preferred pressure in the range of from about 10 to about 1,000 psig.

The ester hydrolysis catalyst is a conventional material and can be selected from an acidic catalyst such as acidic ion-exchange resins, acidic gamma alumina, fluorinated alumina, sulfate or tungstate promoted zirconia, titania or silica promoted alumina, aluminum phosphate, tungsten oxide supported on silica-alumina, clays, supported mineral acids, zeolites, or heteropoly acids. Acidic zeolites such as Y, X, A, ZSM types, and mordenite in either their protonated or partially exchanged forms are particularly useful. Use of dealuminated zeolites or zeolites with inherently high Si/Al ratios may provide additional benefits. The term heteropoly acid includes both fully protonated and partially exchanged salts such as $H_3PO_4W_{12}O_{36}$, $Cs_1H_2PO_4W_{12}O_{36}$, and $Cs_{2.5}H_{0.5}PO_4W_{12}O_{36}$. Other heteropoly acids which could be suitable include tungstosilicates, tungstovanadates, molybdosilicates, molybdophosphates, niobotungstates, molybdovanadates, and the like. The heteropoly acids may be supported on a carrier such as silica, titania, carbon, and the like. More generally, the acid forms of heteropoly and isopoly oxometalates are useful for this invention. A detailed discussion of these materials is provided by Pope in "Heteropoly and Isopoly Oxometallates", Springer-Verlag, 1983.

With reference to FIGS. 6 and 7, the ester hydrolysis reaction is coupled with the alcohol dehydration reaction. The temperature in the ester hydrolysis/alcohol dehydration reaction zone is selected from the range of from about 50° C. to about 400° C., preferably a temperature in the range of from about 100° C. to about 350° C. The feed rate sent to the ester hydrolysis/alcohol dehydration reactor can vary significantly, depending upon a variety of factors such as, for example, reaction conditions, composition of the feedstock and quantity and type of catalyst being used. The liquid hourly space velocity (LHSV) to the ester hydrolysis/alcohol dehydration reactor when the feed is vaporized prior to entering or within the reactor may range from about 0.001 to about 100 $hr^{-1}$, preferably from about 0.01 to about 10 $hr^{-1}$. The pressure in the ester hydrolysis/alcohol dehydration reaction zone may be selected from the range of from about 1 to about 10,000 psig, preferably a pressure in the range of from about 10 to about 5,000 psig, with an especially preferred pressure in the range of from about 10 to about 1,000 psig.

The ester hydrolysis catalyst and alcohol dehydration catalyst can the same or different and both are described above. In this coupled arrangement, the catalysts can be configured as a single bed or layered or intimate mixture.

Reactive Distillation

The reactive distillations useful in this invention can employ conventional techniques. The ester hydrolysis/ alcohol dehydration reactive distillation can be carried out by passing an ester and ether over one or more catalysts as a vapor phase reaction or as a liquid phase reaction, e.g., slurry reaction. The ester hydrolysis reactive distillation and alcohol dehydration reactive distillation may be conducted either alone or in combination, e.g., coupled as in FIG. 8 or decoupled as in FIG. 9. In both configurations, the water formed from the alcohol dehydration can be used to drive the ester hydrolysis. In a preferred embodiment, methyl acetate can be converted into acetic acid and methanol can be converted to dimethyl ether.

With reference to FIGS. 8–9, the temperature in the ester hydrolysis reactive distillation zone and alcohol dehydration reactive distillation zone (either alone or in combination) is selected from the range of from about 100° C. to about 500° C., preferably a temperature in the range of from about 150° C. to about 400° C. The feed rate of the feedstock sent to the reactive distillation column(s) can vary significantly, depending upon a variety of factors such as, for example, reaction conditions, composition of the feedstock and quantity and type of catalyst being used. The pressure in the ester hydrolysis reactive distillation zone and alcohol dehydration reactive distillation zone (either alone or in combination) may be selected from the range of from about 1 to about 1000 psig, preferably a pressure in the range of from about 50 to about 500 psig.

The ester hydrolysis catalyst and alcohol dehydration catalyst used in the reactive distillations can the same or different and both are described above. In a coupled arrangement, the catalysts can be configured as a single bed or layered or intimate mixture.

In the embodiment of this invention which involves converting a feedstock comprising at least one alcohol, ether, or mixtures thereof to a product stream comprising at least one of an ester, acid, acid anhydride and mixtures thereof, suitable feedstocks may include, for example, mono- and polyhydric alcohols, alkylethers such as alkyl or alkylene mono- and polyethers, and alkyl ether alcohols and mixtures thereof. Such compounds may contain aromatic rings. The preferred alcohols and ethers and that may be carbonylated by the processes of this invention include alkanols of 1 to about 20 carbon atoms, alkane polyols of 2 to about 24 carbon atoms, alkyl monoethers of 2 to about 20 carbon atoms, alkyl alkylene polyethers of 4 to about 40 carbon atoms and alkoxyalkanols of 3 to about 20 carbon atoms. Illustrative alcohols and ethers that may be carbonylated in accordance with this invention are disclosed in U.S. Pat. Nos. 5,218,140 and 5,330,955, the disclosures of which are incorporated herein by reference. The feedstocks comprising at least one alcohol, ether, or mixtures thereof may be prepared as described herein or alternatively may be obtained from a different source and fed directly or indirectly to the carbonylation catalyst.

The catalysts and catalytic components of this invention may be utilized with or without support. The catalysts and catalytic components may be present in the reactors in any of a variety of forms. They may be present as a physical admixture or blend of each of the catalytic components, a uniform catalyst prepared by known co-precipitation techniques, continuous or discontinuous portions or layers of the different components impregnated into or coated on a support, or as staggered, alternating or, simply, distinct portions of the different components placed within the reactor.

The use of heterogeneous alcohol carbonylation catalysts or alcohol carbonylation catalytic components as described herein permits the reaction to proceed without the addition of a halide, e.g., iodide, promoter, such as $CH_3I$ in methanol carbonylation and/or HI which are highly corrosive, necessitate the use of expensive corrosion resistant materials of construction and require extensive separation procedures to remove the iodide from the product stream.

The processes and catalysts of this invention enable the production of oxygenates at desirable reaction rates and selectivities. Reaction rates are not narrowly critical and preferably are at least about 0.5 pounds of product per cubic foot of catalyst per hour (0.5 lb/ft3 cat/hr) and more preferably at least about 1.0 lb/ft3 cat/hr. Product selectivities (excluding unreacted feeds) are not narrowly critical and preferably are at least about 25 percent and more preferably at least about 50 percent of the desired product. The particular reaction rates and selectivities will be governed by the best compromise between achieving high catalyst selectivity, lifetime and ease of operability, as well as the intrinsic reactivity of the starting materials and the stability of the starting materials and the desired reaction product to the reaction conditions.

In addition to the methods described above, recovery and purification of desired products may be accomplished by any appropriate means. The desired products of this invention may be recovered in any conventional manner and one or more separators or separation zones may be employed in any given process to recover the desired reaction product from its crude reaction product. Suitable separation and purification methods include, for example, distillation, phase separation, extraction, absorption, crystallization, membrane, derivative formation and the like. The processes of this invention may involve one or more recycle procedures. Gas and/or liquid recycle procedures may be employed as appropriate.

The reactors described with reference to FIGS. 1–14 may be tube and shell design reactors, wherein the catalyst is a fixed bed catalyst and the reaction takes place in the vapor phase. Other types of reactions and, correspondingly, reactors that can be used include a fluidized bed, where the solid catalyst system is fluidized by the incoming gas stream, a slurry reactor where the catalyst is insoluble in the reaction media, or a bubble column reactor. When acetic acid is the desired product, it will be the most corrosive component in the reactor and refining system so the material of construction for the reactor and refining system may only be stainless steel, a relatively inexpensive material as compared to the exotic materials, such as Hastelloy C or zirconium clad Hastelloy, used in commercial processes employing a homogeneous iodide-promoter.

The processes of this invention may be carried out using, for example, a fixed bed reactor, a fluid bed reactor, a continuous stirred tank reactor (CSTR) or a slurry reactor. The optimum size and shape of the catalysts will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low.

The processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the materials present during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials. When complete conversion is not desired or not obtainable, the starting materials can be separated from the product and the starting materials then recycled back into the reaction zone.

For purposes of this invention, the chemical elements are identified in accordance with the Periodic Table of the Elements reproduced in "Hawley's Condensed Chemical Dictionary" 12$^{th}$ Edition, Revised by Richard J. Lewis, Sr., Van Nostrand Reinhold Company, New York, 1993.

The following examples are intended to demonstrate the unexpected advantages, uniqueness and superiority of the invention as compared to the prior art.

EXAMPLE 1

This example demonstrates the feasibility of the scheme depicted by FIG. 1. The reaction system consists of a feed system, a fixed bed reactor, and an on-line analyzer. The system is capable of high temperature and high pressure operation. In the feed system, a synthesis gas feedstock is first passed through an activated carbon trap to remove metal carbonyl contaminants. The purified feedstock then passes through a mass flow meter and into the reaction tube inlet. The reaction tube is stainless steel and is heated with an air fluidized sand bath. The gas product stream exiting the reactor enters into an analytical section equipped with switching valves that provide 0.6 milliliter reactor off-gas samples that are analyzed in a Varian 3700 gas chromatograph equipped with two detectors. $H_2$, $N_2$, CO and $CO_2$ are separated on a 10', ⅛", 80/100 Carbosieve S-2 column purchased from Supelco and detected by thermal conductivity. All organic products are resolved on a 12', ⅛", 80/100 Tenax column obtained from Alltech and detected using flame ionization. Argon is used as the carrier gas for both columns.

A reactor tube was first charged with quartz beads followed by 1.0 gram of a Cu—Zn oxide methanol synthesis catalytic component available from United Catalysts (United Catalyst No. 2537-S) that was bulk mixed with 2 grams of quartz beads. This catalytic component was reduced at 270° C. in a 5%$H_2$/95%$N_2$ stream for 6 hours.

As the heterogeneous alcohol carbonylation catalytic component an iridium and palladium exchanged $H_3W_{12}PO_{40}$ heteropoly acid catalytic component was used. The component was prepared as follows: Pd(NO$_3$)$_2$ (0.23 grams) and IrCl$_3$.3H$_2$O (0.37 grams) were added to 50 milliliters of degassed methanol under $N_2$ in a Schlenk flask and stirred for 0.5 hour. Next, $H_3W_{12}PO_{40}$ (6.50 grams) was added and the mixture was stirred for an additional 1 hour. Activated Grade 12 silica gel (SiO$_2$) was added and the slurry stirred for 4 hours. The methanol was then removed at 80° C., under vacuum, yielding Ir—Pd—$H_3W_{12}PO_{40}$—$SiO_2$. This catalytic component has essentially the same composition reported for Example 17 of U.S. Pat. No. 5,330,955, where the mole ratio of M1:M2:$H_3W_{12}PO_{40}$ is approximately 1:1:2 with M1 being iridium and M2 being palladium.

The reactor tube was opened and 2.069 grams of Ir—Pd—$H_3W_{12}PO_{40}$—$SiO_2$ mixed with 2 grams of quartz beads was added to Cu—Zn oxide methanol catalytic component in the reactor. The reactor tube was then connected to the reaction system and the entire system flushed with nitrogen. The reactor bed was packed in such a way that the incoming synthesis gas first contacted the Cu—Zn catalytic component, and then the reaction stream contacted the Ir—Pd—$H_3W_{12}PO_{40}$—$SiO_2$.

The reaction zone was maintained at a uniform temperature of about 235° C. and a uniform pressure of about 1000 psig with the synthesis gas having a hydrogen to carbon monoxide molar ratio of 1:1. The GHSV of the syn gas fed to the reactor was 6000/hr. After 16 hours of reaction a sample of the reaction menstruum was analyzed. The analysis showed the carbon monoxide conversion was about 5% and the reaction product distribution was $CH_4$=15.1%, $C_2H_6$=4.1%, $CH_3OH$=62.1%, and $CH_3COOH$=17.5%.

The catalyst was relatively stable over the test period of 168 hours. The stability of the catalyst was surprising because the heterogeneous alcohol carbonylation catalytic compound significantly deactivated after 8 hours when only methanol and carbon monoxide were fed to the reactor. The presence of hydrogen and/or synthesis gas in the reactor is believed to contribute to the unexpected increase in stability of the heterogeneous alcohol carbonylation catalytic component of the catalyst.

EXAMPLE 2

This example demonstrates the feasibility of the scheme depicted by FIG. 4. The following reactions were carried out in a ⅜" 316 stainless steel reactor tube capable of high pressure operation. The reactor was housed in a convection oven. Synthesis gas was supplied to the reactor under pressure, as was any liquid feed. The product stream exiting the reactor was maintained as a vapor and sent to an online gas chromatography for analysis. Regarding reactor tube loading, a reactor tube was first charged with quartz beads followed by 2 to 3 grams of the carbonylation catalyst mixed with 2 grams of quartz beads. The reactor tube was then connected to the reaction system and the entire system was well flushed with nitrogen. The gas feed was switched to synthesis gas and the reaction system brought to operating conditions. Liquid feed was then added. Table A below contains data for various catalysts used to carbonylate methanol to methyl acetate or a mixture of methyl acetate and acetic acid. For all examples, the reaction was carried out at 1000 psig with the indicated hydrogen:carbon monoxide gas feed. Methanol was fed to the reactor as a neat liquid at the reported LHSV. The results are set forth in Table A. Each catalyst contained 0.1 wt % Pd.

TABLE A

| Catalyst | Pd—ZrO$_2$—WO$_3$ | Pd—ZrO$_2$—WO$_3$ | Pd—ZrO$_2$—WO$_3$ |
|---|---|---|---|
| Temperature, ° C. | 335 | 355 | 350 |
| Pressure, psig | 1000 | 1000 | 1000 |
| Feed composition, mole % | | | |
| H$_2$ | 49.1 | 38.4 | 39.4 |
| CO | 47.2 | 38.4 | 39.4 |
| methanol | 3.7 | 23.2 | 21.2 |
| Inlet GHSV, hr$^{-1}$ | 12000 | 14180 | 15000 |
| Inlet LHSV, hr$^{-1}$ | 1.5 | 7.1 | 6.67 |
| Product stream composition, mole % | | | |
| dimethyl ether | 10.8 | 18.7 | 30.17 |
| methanol | 19.2 | 16.4 | 21.35 |
| methyl acetate | 15.7 | 10.9 | 16.52 |
| acetic acid | 18.3 | 5.9 | 5.04 |
| methane | 28.4 | 33.3 | 21.61 |
| ethane | 0.4 | 2.6 | 1.52 |
| ethylene | 0 | 0 | 0.1 |
| propylene | 0 | 0 | 0.4 |
| propane | 0 | 1.3 | 1.1 |
| butane | 0.7 | 0.8 | 1 |
| carbon dioxide | 5.8 | 10.1 | 1 |
| Rate, lb/ft$^3$-cat hr | | | |
| acetic acid | 9.7 | 20.14 | 15.29 |
| methyl acetate | 10.3 | 45.5 | 61.79 |
| MeOH conversion, % | 68.9 | 72.1 | 40 |
| CO conversion, % | 7.1 | 26.8 | 30.4 |

EXAMPLE 3

This example demonstrates the feasibility of the scheme depicted in FIG. 4 with a feed gas molar ratio of carbon monoxide:hydrogen of 90:10. The catalyst was prepared by impregnating ⅛" extrudates of ZrO$_2$—WO$_3$, obtained from Norton Corp. (Akron, Ohio), via incipient wetness with an aqueous solution of Pd (NO$_3$)$_2$ and NH$_4$Cl. The catalyst was air dried at 23° C. for 1 hour, 65° C. for 1 hour, and finally 120° C. for 4 hours. The catalyst was then calcined in air at 450° C. for 8 hours. The final catalyst, based on the initial amounts of starting materials, contained 0.05 wt % Pd and 0.1 wt % Cl. The reaction was conducted according to the procedures described in Example 2. The reaction conditions were as follows: temperature of 325° C., GHSV of 9,000 hr$^{-1}$, carbon monoxide:hydrogen molar ratio of 90:10 and methanol LHSV of 1.5 hr$^{-1}$. The results are reported in Table B below after 24 hours on stream.

TABLE B

| | Selectivity wt % |
|---|---|
| Product stream composition (excludes methanol and dimethyl ether) | |
| MeOAc | 80.25 |
| HOAc | 8.69 |
| CH$_4$ | 5.71 |
| Ethane | 0.40 |
| Ethylene | 0.15 |
| Propane | 0 |

TABLE B-continued

| | Selectivity wt % |
|---|---|
| Propene | 0.48 |
| Butane | 0.90 |
| CO$_2$ | 3.42 |
| Productivity, lb/ft$^3$ cat/hr | |
| MeOAc | 26.3 |
| HOAc | 3.5 |

EXAMPLE 4

This example demonstrates the feasibility of the scheme depicted by FIG. 5. The bottoms fraction from liquid/gas separator 30 is fed via line 4 to tray 3 of a 15 tray crude ester atmospheric distillation column 40. The crude ester distillation column 40 is run at a reflux ratio of 1.5. The overhead from crude ester distillation column 40 is sent via line 13 to hydrolysis reactor 50 where more water is added. This water is recycled from the tails of extractor column 70. The tails from the crude ester distillation column 40 are fed via line 6 to stage 10 of a 20 stage alcohol, e.g., methanol, distillation column 60. This column is run at a reflux ratio of 3. The tails from alcohol distillation column 60 are fed via line 8 to the top of a 10 stage extractor column 70 in which diethyl ketone is the extractant. The overhead from the extractor column 70 is fed via line 9 to the 15$^{th}$ tray of a 30 tray atmospheric solvent recovery column 80. The overhead from solvent recovery column 80 has a water and organic phase. The water phase reflux ratio is 1, and the organic phase reflux ratio is 2.3. High purity acetic acid (13) is taken from the tails of solvent recovery column 80. With reference to FIG. 5, the composition of various process streams (weight percent) is given in Table C below.

TABLE C

| Stream # | 4 | 6 | 8 | 12 | 9 | 10 | 11 | 7 |
|---|---|---|---|---|---|---|---|---|
| flow, lb/hr | 7493 | 11671 | 8572 | 11284 | 16058 | 5433 | 1635 | 3098 |
| mass fraction | | | | | | | | |
| water | 0.279 | 0.407 | 0.554 | 0.029 | 0.108 | 0.873 | 0.86 | 0.0 |
| MA | 0.494 | 0.033 | 0 | 0 | 0 | 0 | 0 | 0.12 |
| methanol | 0.153 | 0.242 | 0.013 | 0.013 | 0.012 | 0.021 | 0.027 | 0.88 |
| acetic | 0.074 | 0.318 | 0.433 | 0.043 | 0.243 | 0.075 | 0.073 | 0.0 |
| DEK | | | | 0.916 | 0.637 | 0.03 | 0.04 | 0 |

The base temperatures of the crude ester distillation column 40, alcohol distillation column 60 and solvent recovery column 80 are given in Table D below. All columns run at atmospheric pressure. The operating pressure is not critical to this scheme. Operating temperatures and equipment size will vary with the design pressure.

TABLE D

| Crude ester distillation column base | 82° C. | 1 atm |
|---|---|---|
| Alcohol distillation column base | 99° C. | 1 atm |
| Solvent recovery column base | 118° C. | 1 atm |

EXAMPLE 5

This example demonstrates the feasibility of the scheme depicted by FIG. 7. Stream 14 is fed to a hydrolysis/dehydration reactor 50 operated at 300° C. and 200 psi. The product from this reactor is fed via line 32 to the ether (dimethyl ether) stripper column 60 at tray 10 of a 15 theoretical tray distillation column operated at 200 psia. The reflux ratio of this ether stripper column is 6. The tails of the ether stripper column is fed to a refining column 40 at tray 10 of 15 theoretical trays. The reflux ratio is 0.3 and this refining column is operated at 90 psia. High purity acetic acid is recovered in this product steam 22. The distillate from the refining column 40 is recycled via line 17 to the hydrolysis/dehydration reactor 50. The composition of various process streams is given in Table E below.

TABLE E

| Stream Number | 14 | 32 | 28 | 16 |
|---|---|---|---|---|
| Flow, pph | 76594 | 559566 | 511261 | 48305 |
| Mass Fraction: | | | | |
| Water | | 0.047 | 0.051 | |
| MeAc | 0.977 | 0.672 | 0.735 | |
| Acetic Acid | | 0.108 | 0.119 | |
| DME | 0.023 | 0.144 | 0.063 | 1.0 |
| Methanol | | 0.029 | 0.032 | |

EXAMPLE 6

This example demonstrates the feasibility of the scheme depicted by FIG. 8. The reactive distillation column 30 has a 35 theoretical stages with a reactive zone from stage 10 to stage 30. The reactive column is operated at 200 psia and has a reflux ratio of 5. Methyl acetate is fed on stage 20 and methanol is fed on stage 10. A small amount of excess water is fed via line 3 to stage 19 to increase conversion of the methyl acetate to acetic acid. The reactive distillation column 30 is capable of producing a stream of dimethyl ether with small amount of methyl acetate and methanol to recycle to the carbonylation reactor and a wet stream of acetic acid in the base. It is believed that each reactive stage is at chemical equilibrium with respect to the reaction of alcohol and carboxylic acid to produce the ester and water and the reaction of the alcohol to produce the ether and water. The composition of various process streams is given in Table F below.

TABLE F

| Stream Number | 42 | 3 | 26 | 27 |
|---|---|---|---|---|
| Flow, pph | 76595 | 901 | 61002 | 48215 |
| Mass Fraction: | | | | |
| Water | | 1.0 | 0.012 | |
| MeAc | 0.977 | | | 0.01 |
| Acetic Acid | | | 0.988 | |
| DME | 0.023 | | | 0.987 |
| Methanol | | | | 0.003 |

The foregoing description of the preferred embodiments of this invention and the examples are presented for purposes of best teaching one skilled in the art how to practice the invention. It is not, nor is it intended to be, an exhaustive description of every permutation of the invention. Obviously, many variations and modifications are possible in light of the disclosure and readily apparent to a person of ordinary skill in the art to which this invention pertains. It is intended that the full scope of the invention be defined by the appended claims.

What is claimed is:

1. A process for converting a feedstock stream comprising at least one of an alcohol and ether and mixtures thereof to a product stream comprising at least one of an ester, acid, acid anhydride and mixtures thereof which comprises (a) feeding at least a portion of a first feedstock stream comprising carbon monoxide and a second feedstock stream comprising an alcohol and/or ether to a carbonylation reaction zone, (b) reacting in said carbonylation reaction zone the first and second feedstock streams in the presence of a catalyst comprising a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, or mixtures thereof, and in the absence of a halide promoter, under conditions of temperature and pressure sufficient to produce a first crude product stream comprising at least one of an ester, acid, acid anhydride, alcohol, ether, water and mixtures thereof, (c) withdrawing said first crude product stream and unreacted carbon monoxide from said carbonylation reaction zone and feeding at least a portion of the withdrawn stream and carbon monoxide to a liquid/gas separation zone, (d) withdrawing from the liquid/gas separation zone an overhead fraction comprising said carbon monoxide and optionally recycling at least a portion of the withdrawn overhead fraction to said carbonylation reaction zone, (e) withdrawing from the liquid/gas separation zone a bottoms fraction comprising said first crude product stream and feeding at least a portion of the withdrawn bottoms fraction to a distillation zone, (f) withdrawing from the distillation zone an overhead fraction comprising an ester and feeding at least a portion of the withdrawn overhead fraction to a hydrolysis reaction zone, (g) reacting in the hydrolysis reaction zone in the presence of an ester hydrolysis catalyst said withdrawn overhead fraction under conditions of temperature and pressure sufficient to produce a second crude product stream comprising at least one of an ester, acid, acid anhydride, alcohol, ether, water and mixtures thereof, (h) withdrawing from the hydrolysis reaction zone said second crude product stream and feeding at least a portion of the withdrawn stream to said distillation zone, (i) optionally withdrawing from the distillation zone a sidedraw fraction comprising an alcohol and/or ether and feeding at least a portion of the withdrawn sidedraw fraction to said carbonylation reaction zone, and (j) withdrawing from the distillation zone a bottoms fraction comprising said product stream.

2. A process for converting a feedstock stream comprising at least one of an alcohol and ether and mixtures thereof to a product stream comprising at least one of an ester, acid, acid anhydride and mixtures thereof which comprises (a) feeding at least a portion of a first feedstock stream comprising carbon monoxide and at least a portion of a second feedstock stream comprising an alcohol and/or ether to a carbonylation reaction zone, (b) reacting in said carbonylation reaction zone the carbon monoxide and alcohol and/or ether in the presence of a catalyst comprising a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, or mixtures thereof, and in the absence of a halide promoter, under conditions of temperature and pressure sufficient to produce a first crude product stream comprising at least one of an ester, acid, acid anhydride, alcohol, ether, water and mixtures thereof, (c) withdrawing said first crude product stream and unreacted carbon monoxide from said carbonylation reaction zone and feeding at least a portion of the withdrawn stream and carbon monoxide to a liquid/gas separation zone, (d) withdrawing from the liquid/gas separation zone an overhead fraction comprising said carbon monoxide and optionally recycling at least a portion of the withdrawn overhead fraction to said carbonylation reaction zone, (e) withdrawing from the liquid/gas separation zone a bottoms fraction comprising said first crude product stream and feeding at least a portion of the withdrawn bottoms fraction to a hydrolysis/dehydration reaction zone, (f) reacting in the hydrolysis/dehydration reaction zone in the presence of a catalyst comprising an ester hydrolysis catalytic component and an alcohol dehydration catalytic component said first crude product stream under conditions of temperature and pressure sufficient to produce a second crude product stream comprising at least one of an ester, acid, acid anhydride, alcohol, ether, water and mixtures thereof, (g) withdrawing from the hydrolysis/dehydration reaction zone said second crude product stream and feeding at least a portion of the withdrawn stream to a distillation zone, (h) withdrawing from the distillation zone an overhead fraction comprising at least one ether and optionally recycling at least a portion of the withdrawn overhead fraction to said carbonylation reaction zone, (i) withdrawing from the distillation zone a sidedraw fraction comprising at least one of an ester, acid, acid anhydride, alcohol, water and mixtures thereof and optionally recycling at least a portion of the withdrawn sidedraw fraction to said hydrolysis/dehydration reaction zone, and (j) withdrawing from the distillation zone a bottoms fraction comprising said product stream.

3. A process for converting a feedstock stream comprising at least one of an alcohol and ether and mixtures thereof to a product stream comprising at least one of an ester, acid, acid anhydride and mixtures thereof which comprises (a) feeding at least a portion of a first feedstock stream comprising carbon monoxide to a carbonylation reaction zone, (b) feeding at least a portion of a second feedstock stream comprising an alcohol and/or ether to a hydrolysis/dehydration reaction zone, (c) reacting in a carbonylation reaction zone the carbon monoxide stream and an ether-rich stream from an ether separation zone in the presence of a catalyst comprising a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, or mixtures thereof, and in the absence of a halide promoter, under conditions of temperature and pressure sufficient to produce a first crude product stream comprising at least one of an ester, acid, acid anhydride, alcohol, ether, water and mixtures thereof, (d) withdrawing said first crude product stream and unreacted carbon monoxide from said carbonylation reaction zone and feeding at least a portion of the withdrawn stream and carbon monoxide to a liquid/gas separation zone, (e) withdrawing from the liquid/gas separation zone an overhead fraction comprising said carbon monoxide and optionally recycling at least a portion of the withdrawn overhead fraction to said carbonylation reaction zone, (f) withdrawing from the liquid/gas separation zone a bottoms fraction comprising said first crude product stream and feeding at least a portion of the withdrawn bottoms fraction to said hydrolysis/dehydration reaction zone, (g) reacting in the hydrolysis/dehydration reaction zone in the presence of a catalyst comprising an ester hydrolysis catalytic component and an alcohol dehydration catalytic component said withdrawn bottoms fraction comprising a mixture of an alcohol and ether under conditions of temperature and pressure sufficient to produce a second crude product stream comprising at least one of an ester, acid, acid anhydride, alcohol, ether, water and mixtures thereof, (h) withdrawing from the hydrolysis/dehydration reaction zone said second crude product stream and feeding at least a portion of the withdrawn stream to said ether separation zone to provide an overhead fraction comprising said ether-rich stream and a bottoms fraction comprising at least one of an ester, acid, acid anhydride, alcohol, water and mixtures thereof, (i) withdrawing from the ether separation zone said overhead fraction and optionally recycling at least a portion of the withdrawn overhead fraction to said carbonylation reaction zone, (j) withdrawing from the ether separation zone said bottoms fraction and feeding at least a portion of the withdrawn bottoms fraction to a distillation zone, (k) withdrawing from the distillation zone an overhead fraction comprising a mixture of an alcohol, ester and ether and feeding at least a portion of the withdrawn overhead fraction to said hydrolysis/dehydration reaction zone, and (l) withdrawing from the distillation zone a bottoms fraction comprising said product stream.

4. A process for converting a feedstock stream comprising at least one of an alcohol and ether and mixtures thereof to a product stream comprising at least one of an ester, acid, acid anhydride and mixtures thereof which comprises (a) feeding at least a portion of a first feedstock stream comprising carbon monoxide to a carbonylation reaction zone, (b) feeding at least a portion of a second feedstock stream comprising an alcohol and/or ether to a reactive distillation zone, (c) reacting in said carbonylation reaction zone the carbon monoxide stream and an ether-containing stream from said reactive distillation zone in the presence of a catalyst comprising a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, or mixtures thereof, and in the absence of a halide promoter, under conditions of temperature and pressure sufficient to produce a crude product stream comprising at least one of an ester, acid, acid anhydride, alcohol, ether, water and mixtures thereof, (d) withdrawing said crude product stream and unreacted carbon monoxide from said carbonylation reaction zone and feeding at least a portion of the withdrawn stream and carbon monoxide to a liquid/gas separation zone, (e) withdrawing from the liquid/gas separation zone an overhead fraction comprising said carbon monoxide and lower boiling byproducts and optionally feeding at least a portion of the withdrawn overhead fraction to a feedstock preparation zone and/or said carbonylation reaction zone, (f) withdrawing from the liquid/gas separation zone a bottoms fraction comprising at least one of an ester, acid, ether, alcohol, water and mixtures thereof and feeding at least a portion of the withdrawn bottoms fraction to said reactive distillation zone, said reactive distillation zone containing a catalyst comprising an ester hydrolysis catalytic component and an alcohol dehydration catalytic component, (g) withdrawing from the reactive distillation zone an overhead fraction comprising said ether-containing stream and feeding at least a portion of the ether-containing stream to said carbonylation reaction zone, and (h) withdrawing from the reactive distillation zone a bottoms fraction comprising said product stream.

5. A process for converting a feedstock stream comprising at least one of an alcohol and ether and mixtures thereof to a product stream comprising at least one of an ester, acid, acid anhydride and mixtures thereof which comprises (a) feeding at least a portion of a first feedstock stream comprising carbon monoxide to a carbonylation reaction zone, (b) feeding at least a portion of a second feedstock stream comprising an alcohol and optionally an ether to a dehydration reactive distillation zone, (c) reacting in said carbonylation reaction zone the carbon monoxide and an ether-containing stream from said dehydration reactive distillation zone in the presence of a catalyst comprising a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, or mixtures thereof, and in the absence of a halide promoter, under conditions of temperature and pressure sufficient to produce a crude product stream comprising at least one of an ester, acid, acid anhydride, alcohol, ether, water and mixtures thereof, (d) withdrawing said crude product stream and unreacted carbon monoxide from said carbonylation reaction zone and feeding at least a portion of the withdrawn stream and carbon monoxide to a liquid/gas separation zone, (e) withdrawing from the liquid/gas separation zone an overhead fraction comprising said carbon monoxide and optionally recycling at least a portion of the withdrawn overhead fraction to said carbonylation reaction zone, (f) withdrawing from the liquid/gas separation zone a bottoms fraction comprising said crude product stream and feeding at least a portion of the withdrawn bottoms fraction to a hydrolysis reactive distillation zone, said hydrolysis reactive distillation zone containing an ester hydrolysis catalyst, (g) withdrawing from the hydrolysis reactive distillation zone an overhead fraction comprising a mixture of an alcohol, ether and ester and feeding at least a portion of the withdrawn overhead fraction to said dehydration reactive distillation zone, said dehydration reactive distillation zone containing an alcohol dehydration catalyst, (h) withdrawing from the dehydration reactive distillation zone an overhead fraction comprising said ether-containing stream and feeding at least a portion of the ether-containing stream to said carbonylation reaction zone, (i) withdrawing from the dehydration reactive distillation zone a bottoms fraction comprising at least one of an acid, ester and water and feeding at least a portion of the withdrawn bottoms fraction to said hydrolysis reactive distillation zone, and (j) withdrawing from the hydrolysis reactive distillation zone a bottoms fraction comprising said product stream.

6. A process for converting a feedstock stream comprising at least one of an alcohol and ether and mixtures thereof to a product stream comprising at least one of an ester, acid, acid anhydride and mixtures thereof which comprises (a) feeding at least a portion of a first feedstock stream comprising carbon monoxide to a carbonylation reaction zone, (b) feeding at least a portion of a second feedstock stream comprising an alcohol and/or ether to a hydrolysis/dehydration reaction zone, (c) reacting in a carbonylation reaction zone the carbon monoxide stream and an ether-rich stream from an ether separation zone in the presence of a catalyst comprising a solid super acid impregnated with a Group 7, 8, 9, 10 and/or 11 metal, a heteropoly acid impregnated with a Group 7, 8, 9, 10 and/or 11 metal, a clay impregnated with a Group 7, 8, 9, 10 and/or 11 metal, a zeolite impregnated with a Group 7, 8, 9, 10 and/or 11 metal or a molecular sieve impregnated with a Group 7, 8, 9, 10 and/or 11 metal, or mixtures thereof, and in the absence of a halide promoter, under conditions of temperature and pressure sufficient to produce a first crude product stream comprising at least one of an ester, acid, acid anhydride, alcohol, ether, water and mixtures thereof, (d) withdrawing said first crude product stream and unreacted carbon monoxide from said carbonylation reaction zone and feeding at least a portion of the withdrawn stream and carbon monoxide to a first lights separation zone, (e) withdrawing from the first lights separation zone an overhead fraction comprising said carbon monoxide and optionally recycling at least a portion of the withdrawn overhead fraction to said carbonylation reaction zone, (f) withdrawing from the first lights separation zone a bottoms fraction comprising said first crude product stream and feeding at least a portion of the withdrawn bottoms fraction to a liquid/gas separation zone, (g) withdrawing from the liquid/gas separation zone an overhead fraction comprising said carbon monoxide and optionally recycling at least a portion of the withdrawn overhead fraction to said carbonylation reaction zone, (h) withdrawing from the liquid/gas separation zone a bottoms fraction comprising said first crude product stream and feeding at least a portion of the withdrawn bottoms fraction to said hydrolysis/dehydration reaction zone, (i) reacting in the hydrolysis/dehydration reaction zone in the presence of a catalyst comprising an ester hydrolysis catalytic component and an alcohol dehydration catalytic component said withdrawn bottoms fraction comprising a mixture of an alcohol and ether under conditions of temperature and pressure sufficient to produce a second crude product stream comprising at least one of an ester, acid, acid anhydride, alcohol, ether, water and mixtures thereof (containing less ester and more acid than said first crude product stream), (j) withdrawing from the hydrolysis/dehydration reaction zone said second crude product stream and feeding at least a portion of the withdrawn stream to a second lights separation zone, (k) withdrawing from the second lights separation zone an overhead fraction comprising at least one of an ether, ester, acid, acid anhydride, alcohol, water and mixtures thereof and feeding at least a portion of the withdrawn overhead fraction to an ether separation zone, (l) withdrawing from the ether separation zone an overhead fraction comprising an ether-rich stream and optionally recycling at least a portion of the withdrawn overhead fraction to said carbonylation reaction zone, (m) withdrawing from the ether separation zone a bottoms fraction comprising at least one of an ester, acid, acid anhydride, alcohol, ether, water and mixtures thereof and and optionally recycling at least a portion of the withdrawn bottoms fraction to said hydrolysis/ dehydration reaction zone, (n) withdrawing from the second lights separation zone a bottoms fraction comprising at least one of an acid, ether, ester, acid anhydride, alcohol, water and mixtures thereof and feeding at least a portion of the withdrawn bottoms fraction to an acid separation zone, (o) withdrawing from the acid separation zone an overhead fraction comprising at least one of an ether, ester, acid anhydride, alcohol, acid, water and mixtures thereof and optionally recycling at least a portion of the withdrawn overhead fraction to said hydrolysis/dehydration reaction zone, and (p) withdrawing from the acid separation zone a bottoms fraction comprising said product stream.

7. The process of claim 1 wherein the second crude product stream contains less ester and more acid than said first crude product stream.

8. The process of claim 2 wherein the second crude product stream contains less ester and more acid than said first crude product stream.

9. The process of claim 3 wherein the second crude product stream contains less ester and more acid than said first crude product stream.

10. The process of claim 1 which is carried out in the presence of hydrogen and/or synthesis gas.

11. The process of claim 2 which is carried out in the presence of hydrogen and/or synthesis gas.

12. The process of claim 3 which is carried out in the presence of hydrogen and/or synthesis gas.

13. The process of claim 4 which is carried out in the presence of hydrogen and/or synthesis gas.

14. The process of claim 5 which is carried out in the presence of hydrogen and/or synthesis gas.

15. The process of claim 6 which is carried out in the presence of hydrogen and/or synthesis gas.

* * * * *